US012435366B2

(12) United States Patent
Wilson et al.

(10) Patent No.: US 12,435,366 B2
(45) Date of Patent: Oct. 7, 2025

(54) MULTIPLE SEQUENCING USING A SINGLE FLOW CELL

(71) Applicant: Lexent Bio, Inc., Cambridge, MA (US)

(72) Inventors: Timothy Wilson, San Diego, CA (US); Haluk Tezcan, San Francisco, CA (US); John Spinosa, San Francisco, CA (US); Alexander Robertson, San Francisco, CA (US); Rohith Srivas, San Francisco, CA (US); Neil Peterman, San Francisco, CA (US); Nicole Lambert, San Francisco, CA (US); Peter George, San Francisco, CA (US); Ram Yalamanchili, San Francisco, CA (US); Kenneth Nesmith, San Francisco, CA (US)

(73) Assignee: Lexent Bio, Inc., Cambridge, MA (US)

( * ) Notice: Subject to any disclaimer, the term of this patent is extended or adjusted under 35 U.S.C. 154(b) by 1284 days.

(21) Appl. No.: 17/263,108

(22) PCT Filed: Jul. 25, 2019

(86) PCT No.: PCT/US2019/043434

§ 371 (c)(1),
(2) Date: Jan. 25, 2021

(87) PCT Pub. No.: WO2020/023744

PCT Pub. Date: Jan. 30, 2020

(65) Prior Publication Data

US 2021/0164038 A1 Jun. 3, 2021

Related U.S. Application Data

(60) Provisional application No. 62/703,763, filed on Jul. 26, 2018.

(51) Int. Cl.
*C12Q 1/6869* (2018.01)
*C12Q 1/6806* (2018.01)

(52) U.S. Cl.
CPC ......... *C12Q 1/6869* (2013.01); *C12Q 1/6806* (2013.01); *C12Q 2535/122* (2013.01)

(58) Field of Classification Search
CPC ............ C12Q 2535/122; C12Q 1/6869; C12Q 1/6806
See application file for complete search history.

(56) References Cited

U.S. PATENT DOCUMENTS 5,409,811 A 4/1995 Tabor et al.
5,674,716 A 10/1997 Tabor et al.
(Continued)

FOREIGN PATENT DOCUMENTS

CN 101641449 A 2/2010
JP 2018512048 A 5/2018
(Continued)

OTHER PUBLICATIONS

Seifuddin, F et al Genome-wide Methyl-Seq analysis of blood-brain targets of glucocorticoid exposure. 2017. Epigenetics. Taylor & Francis. 12: 637-652. (Year: 2017).*
(Continued)

*Primary Examiner* — Gary Benzion
*Assistant Examiner* — Lisa Horth
(74) *Attorney, Agent, or Firm* — MORRISON & FOERSTER LLP

(57) ABSTRACT

The present disclosure provides methods and systems for nucleic acid sequencing. Such systems and methods may use a single flow cell to perform unbiased and/or biased sequencing to generate libraries of nucleic acid molecules. An aspect of the present disclosure provides a method for increasing complexity of a sample for sequencing, the
(Continued)

method comprising: providing a first nucleic acid sample having a first degree of complexity that differs from a desired degree of complexity; providing a second nucleic acid sample having a second degree of complexity that differs from the first degree of complexity and that differs from the desired degree of complexity; pooling at least a portion of the first nucleic acid sample and at least a portion of the second nucleic acid sample, thereby generating a pooled nucleic acid sample having the desired degree of complexity; and sequencing at least a portion of the pooled nucleic acid sample.

21 Claims, 6 Drawing Sheets

(56) References Cited

U.S. PATENT DOCUMENTS

| | | | | |
|---|---|---|---|---|
| 6,593,114 | B1 * | 7/2003 | Kunsch | C12N 15/52 435/254.11 |
| 9,745,614 | B2 | 8/2017 | Schroeder | |
| 2012/0270739 | A1 * | 10/2012 | Rava | C12Q 1/6806 702/20 |
| 2014/0287934 | A1 * | 9/2014 | Szelinger | G16B 30/00 702/19 |
| 2014/0357497 | A1 | 12/2014 | Zhang | |
| 2015/0066824 | A1 | 3/2015 | Harris et al. | |
| 2016/0046987 | A1 | 2/2016 | Kim et al. | |
| 2016/0281166 | A1 | 9/2016 | Bhattacharjee et al. | |
| 2017/0022232 | A1 | 1/2017 | Schrodi | |
| 2017/0088832 | A1 | 3/2017 | McEwan et al. | |

FOREIGN PATENT DOCUMENTS

| | | | |
|---|---|---|---|
| WO | 2006137733 | A1 | 12/2006 |
| WO | WO-2012149171 | A1 | 11/2012 |
| WO | 2016022540 | A1 | 2/2016 |
| WO | 2016127944 | A1 | 8/2016 |
| WO | 2020023744 | A1 | 1/2020 |

OTHER PUBLICATIONS

Roeh, S. et al. (2017, e-pub. Jun. 8, 2017). "Sequencing On The SOLiD 5500xl System—In-Depth Characterization Of The GC Bias," Nucleus 8(4):370-380, 12 pages.

Wang, X. et al. (2014). "The Application Of DNA Pooling And Pyrosequencing On Detecting Gene Frequencies In Association Study," Chinese Journal of Eugenics and Genetics 22(12):7-11 [English Abstract].

Aird et al., (2011). "Analyzing and minimizing PCR amplification bias in Illumina sequencing libraries," Genome Biology, 12:R18, p. 1-14.

Extended European Search Report received for European Patent Application No. 19840946.8 mailed on Mar. 30, 2022, 7 pages.

International Search Report and Written Opinion received for PCT Patent Application No. PCT/US2019/043434, mailed on Dec. 5, 2019, 11 pages.

Tabor et al., (1989). "Effect of manganese ions on the incorporation of dideoxynucleotides by bacteriophage T7 DNA polymerase and *Escherichia coli* DNA polymerase I," PNAS, 86:4076-4080.

Illumina, (2016). "Using a PhiX Control for HiSeq® Sequencing Runs," available online at <https://www.illumina.com/content/dam/illumina-support/documents/products/technotes/technote_phixcontrolv3.pdf>, 2 pages.

Illumina, (2017). "An Introduction to Next-Generation Sequencing Technology," Advances in Sequencing Technology "Multiplexing," available online at <https://www.illumina.com/content/dam/illumina-marketing/documents/products/illumina_sequencing_introduction.pdf>, 16 pages.

MyIllumina: Support Bulletin, (2015). "Best Practices for Low Diversity Sequencing on the NextSeq System," available online at <https://www.well.ox.ac.uk/ogc/wpcontent/uploads/2017/09/MyIllumina_-Support-Bulletin-Best-Practices-for-Low-Diversity-Sequencing-on-the-NextSeq-System.pdf>, 1 page.

Search Report and Written Opinion received for Singaporean Patent Application No. 11202100570Y, completed on Sep. 27, 2022, 12 pages.

* cited by examiner

MULTIPLE SEQUENCING USING A SINGLE FLOW CELL

CROSS-REFERENCE TO RELATED APPLICATIONS

This application is a national stage application under 35 U.S.C. § 371 of International Application No. PCT/US2019/043434, filed Jul. 25, 2019, which claims the benefit of U.S. Provisional Patent Application No. 62/703,763, filed Jul. 26, 2018, each of which is hereby incorporated by reference in its entirety.

BACKGROUND OF THE INVENTION

The desire to map the human genome has created an interest in technologies for rapid nucleic acid sequencing. Sequencing the first human genome, however, cost about $1 billion and took more than 10 years to complete. Though there have been advances in technology associated with nucleic acid sequencing, large-scale genome projects remain expensive. For example, whole genome sequencing can cost thousands of dollars and may pose prohibitive costs to genomics research projects. Additionally, efficiently utilizing the capacity of sequencing systems may remain a challenge.

SUMMARY OF THE INVENTION

Despite developments in technology, whole genome sequencing may remain costly. Recognizing a need for efficient and/or high-throughput whole genome sequencing approaches, the present disclosure provides methods and systems for nucleic acid sequencing. Such systems and methods may use a single flow cell to perform unbiased and/or biased sequencing to generate libraries of nucleic acid molecules.

A method of biasing specific regions of the genome may be employed in order to enhance the confidence in the sequencing output for areas with relatively greater importance toward assessment or management (e.g., diagnosis, prognosis, treatment selection, treatment monitoring, monitoring for recurrence) of certain diseases while reducing the cost of sequencing on a per sample basis. However, this increased bias may also reduce the complexity of the sequenced sample, which may lead to difficulties for the sequencer in calling individual bases of the genome. In order to overcome this issue, a smaller, well-characterized control genome of the Phi X 174 bacteriophage may be run as a small percentage of total reads available along with the biased samples of interest in order to increase overall complexity of the sequencing run. However, by using this bacteriophage control, some small portion of the total available sequencing reads may be lost toward performing sequencing of this control genome.

The present disclosure provides a method whereby a user may recover this lost sequencing capacity while maintaining the sequencing complexity required for optimal sequencing run quality. An unbiased sample(s) sequenced along with a biased sample(s) may allow the user to make use of the capacity typically lost to the processing of the control genome. This may provide users the ability to run multiple assays in parallel, thus improving sequencing efficiency and/or throughput, thereby saving on overall sequencing cost and time, while still maintaining the sample complexity required for a successful sequencing run.

Additionally, the availability of commercially available sequencers may place constraints on what assays may be economically run on those sequencing instruments. For example, a model designed for higher sequencing output may be too costly to run for biased sequencing applications without multiplexing a large number of specimens in a single run, yet can meaningfully decrease the cost per base for unbiased sequencing runs. The ability to combine both biased and unbiased specimens into a single sequencing run may make the use of higher output instruments more versatile, as they can then be used across a broader spectrum of applications with a reduced run cost per specimen.

An aspect of the present disclosure provides a method for increasing complexity of a sample for sequencing, the method comprising: providing a first nucleic acid sample having a first degree of complexity that differs from a desired degree of complexity; providing a second nucleic acid sample having a second degree of complexity that differs from the first degree of complexity and that differs from the desired degree of complexity; pooling at least a portion of the first nucleic acid sample and at least a portion of the second nucleic acid sample, thereby generating a pooled nucleic acid sample having the desired degree of complexity; and sequencing at least a portion of the pooled nucleic acid sample.

In some embodiments, the sequencing comprises whole genome sequencing (WGS). In some embodiments, the sequencing comprises massively parallel sequencing. In some embodiments, the sequencing comprises sequencing on a sequencing platform that comprises an output of at least about 1 billion reads per flow cell. In some embodiments, the sequencing comprises sequencing on a sequencing platform that comprises an output of at least about 1.5 billion reads per flow cell. In some embodiments, the sequencing comprises sequencing on a sequencing platform that comprises an output of at least about 2 billion reads per flow cell.

Another aspect of the present disclosure provides a method for sequencing nucleic acid molecules, comprising: processing a first plurality of nucleic acid molecules to generate a first plurality of libraries for performing an unbiased sequencing; processing a second plurality of nucleic acid molecules to generate a second plurality of libraries for performing a biased sequencing; pooling the first plurality of libraries and the second plurality of libraries to generate a pooled plurality of libraries; and using a single flow cell of a sequencing platform, sequencing the pooled plurality of libraries to generate a first plurality of sequencing reads corresponding to the first plurality of nucleic acid molecules and a second plurality of sequencing reads corresponding to the second plurality of nucleic acid molecules.

In some embodiments, the unbiased sequencing comprises whole genome sequencing (WGS). In some embodiments, the unbiased sequencing is performed at a depth of no more than about 0.1×, no more than about 0.5×, no more than about 1×, no more than about 2×, no more than about 3×, no more than about 4×, no more than about 5×, no more than about 6×, no more than about 7×, no more than about 8×, no more than about 9×, no more than about 10×, no more than about 12×, no more than about 14×, no more than about 16×, no more than about 18×, no more than about 20×, no more than about 22×, no more than about 24×, no more than about 26×, no more than about 28×, or no more than about 30×. In some embodiments, the biased sequencing comprises targeted sequencing of a target capture panel comprising a plurality of genetic loci. In some embodiments, the targeted sequencing comprises targeted methyl-seq. In some embodiments, the unbiased sequencing comprises methylation sequencing. In some embodiments, the methylation sequencing comprises bisulfite sequencing, whole genome bisulfite sequencing (WGBS), APOBEC-seq, methyl-CpG-binding domain (MBD) protein capture, methyl-DNA immunoprecipitation (MeDIP), methylation sensitive restriction enzyme sequencing (MSRE/MRE-Seq or Methyl-Seq), oxidative bisulfite sequencing (oxBS-Seq), reduced representative bisulfite sequencing (RRBS), or Tet-assisted bisulfite sequencing (TAB-Seq). In some embodiments, generating the second plurality of sequencing reads comprises using at least a portion of the first plurality of libraries as control libraries. In some embodiments, the method further comprises pooling a third plurality of libraries to generate the pooled plurality of libraries, wherein the third plurality of libraries comprises control libraries for generating the first plurality of sequencing reads or the second plurality of sequencing reads. In some embodiments, the first plurality of nucleic acid molecules and the second plurality of nucleic acid molecules comprise DNA molecules. In some embodiments, the first plurality of nucleic acid molecules and the second plurality of nucleic acid molecules comprise RNA molecules. In some embodiments, the sequencing platform is an Illumina™ sequencer.

Another aspect of the present disclosure provides a method for sequencing nucleic acid molecules, comprising: processing a first plurality of nucleic acid molecules to generate a first plurality of libraries for performing a first biased sequencing; processing a second plurality of nucleic acid molecules to generate a second plurality of libraries for performing a second biased sequencing; pooling the first plurality of libraries and the second plurality of libraries to generate a pooled plurality of libraries; and using a single flow cell of a sequencing platform, sequencing the pooled plurality of libraries to generate a first plurality of sequencing reads corresponding to the first plurality of nucleic acid molecules and a second plurality of sequencing reads corresponding to the second plurality of nucleic acid molecules.

In some embodiments, the first biased sequencing comprises targeted sequencing of a first target capture panel comprising a first plurality of genetic loci, and wherein the second biased sequencing comprises targeted sequencing of a second target capture panel comprising a second plurality of genetic loci.

Another aspect of the present disclosure provides a method for sequencing nucleic acid molecules, comprising: processing a first plurality of nucleic acid molecules to generate a first plurality of libraries for performing a first unbiased sequencing; processing a second plurality of nucleic acid molecules to generate a second plurality of libraries for performing a second unbiased sequencing; pooling the first plurality of libraries and the second plurality of libraries to generate a pooled plurality of libraries; and using a single flow cell of a sequencing platform, sequencing the pooled plurality of libraries to generate a first plurality of sequencing reads corresponding to the first plurality of nucleic acid molecules and a second plurality of sequencing reads corresponding to the second plurality of nucleic acid molecules.

In some embodiments, the first unbiased sequencing comprises whole genome sequencing (WGS), and the second unbiased sequencing comprises methylation sequencing. In some embodiments, the methylation sequencing comprises bisulfite sequencing, whole genome bisulfite sequencing (WGBS), APOBEC-seq, methyl-CpG-binding domain (MBD) protein capture, methyl-DNA immunoprecipitation (MeDIP), methylation sensitive restriction enzyme sequencing (MSRE/MRE-Seq or Methyl-Seq), oxidative bisulfite sequencing (oxBS-Seq), reduced representative bisulfite sequencing (RRBS), or Tet-assisted bisulfite sequencing (TAB-Seq). In some embodiments, the unbiased sequencing is performed at a depth of no more than about 0.1×, no more than about 0.5×, no more than about 1×, no more than about 2×, no more than about 3×, no more than about 4×, no more than about 5×, no more than about 6×, no more than about 7×, no more than about 8×, no more than about 9×, no more than about 10×, no more than about 12×, no more than about 14×, no more than about 16×, no more than about 18×, no more than about 20×, no more than about 22×, no more than about 24×, no more than about 26×, no more than about 28×, or no more than about 30×.

In some embodiments, the nucleic acid molecules are extracted from a sample. In some embodiments, the sample is a biological sample.

In some embodiments, the first plurality of nucleic acid molecules and the second plurality of nucleic acid molecules are generated from a same initial biological sample.

Another aspect of the present disclosure provides a system for sequencing nucleic acid molecules, comprising: a controller comprising one or more computer processors; and a support operatively coupled to the controller; wherein the one or more computer processors are individually or collectively programmed to: direct the processing of a first plurality of nucleic acid molecules to generate a first plurality of libraries for performing an unbiased sequencing; direct the processing of a second plurality of nucleic acid molecules to generate a second plurality of libraries for performing a biased sequencing, direct the pooling the first plurality of libraries and the second plurality of libraries to generate a pooled plurality of libraries; generate, from the pooled plurality of libraries, a first plurality of sequencing reads corresponding to the first plurality of nucleic acid molecules; and generate, from the pooled plurality of libraries, a second plurality of sequencing reads corresponding to the second plurality of nucleic acid molecules.

In some embodiments, the unbiased sequencing comprises whole genome sequencing (WGS) or methylation sequencing. In some embodiments, the methylation sequencing comprises bisulfite sequencing, whole genome bisulfite sequencing (WGBS), APOBEC-seq, methyl-CpG-binding domain (MBD) protein capture, methyl-DNA immunoprecipitation (MeDIP), methylation sensitive restriction enzyme sequencing (MSRE/MRE-Seq or Methyl-Seq), oxidative bisulfite sequencing (oxBS-Seq), reduced representative bisulfite sequencing (RRBS), or Tet-assisted bisulfite sequencing (TAB-Seq). In some embodiments, the biased sequencing comprises targeted sequencing of a target capture panel comprising a plurality of genetic loci. In some embodiments, the targeted sequencing comprises targeted methyl-seq.

Another aspect of the present disclosure provides a system for sequencing nucleic acid molecules, comprising: a controller comprising one or more computer processors; and a support operatively coupled to the controller; wherein the one or more computer processors are individually or collectively programmed to: direct the processing of a first plurality of nucleic acid molecules to generate a first plurality of libraries for performing a first biased sequencing; direct the processing of a second plurality of nucleic acid molecules to generate a second plurality of libraries for performing a second biased sequencing, direct the pooling the first plurality of libraries and the second plurality of libraries to generate a pooled plurality of libraries; generate, from the pooled plurality of libraries, a first plurality of sequencing reads corresponding to the first plurality of nucleic acid molecules; and generate, from the pooled plurality of libraries, a second plurality of sequencing reads corresponding to the second plurality of nucleic acid molecules.

In some embodiments, the first biased sequencing comprises targeted sequencing of a first target capture panel comprising a first plurality of genetic loci, and the second biased sequencing comprises targeted sequencing of a second target capture panel comprising a second plurality of genetic loci.

Another aspect of the present disclosure provides a system for sequencing nucleic acid molecules, comprising: a controller comprising one or more computer processors; and a support operatively coupled to the controller; wherein the one or more computer processors are individually or collectively programmed to: direct the processing of a first plurality of nucleic acid molecules to generate a first plurality of libraries for performing a first unbiased sequencing; direct the processing of a second plurality of nucleic acid molecules to generate a second plurality of libraries for performing a second unbiased sequencing, direct the pooling the first plurality of libraries and the second plurality of libraries to generate a pooled plurality of libraries; generate, from the pooled plurality of libraries, a first plurality of sequencing reads corresponding to the first plurality of nucleic acid molecules; and generate, from the pooled plurality of libraries, a second plurality of sequencing reads corresponding to the second plurality of nucleic acid molecules.

In some embodiments, the first unbiased sequencing or the second unbiased sequencing comprises whole genome sequencing (WGS) or methylation sequencing. In some embodiments, the methylation sequencing comprises bisulfite sequencing, whole genome bisulfite sequencing (WGBS), APOBEC-seq, methyl-CpG-binding domain (MBD) protein capture, methyl-DNA immunoprecipitation (MeDIP), methylation sensitive restriction enzyme sequencing (MSRE/MRE-Seq or Methyl-Seq), oxidative bisulfite sequencing (oxBS-Seq), reduced representative bisulfite sequencing (RRBS), or Tet-assisted bisulfite sequencing (TAB-Seq).

Another aspect of the present disclosure provides a non-transitory computer-readable medium comprising machine-executable code that, upon execution by a computer processor, implements a method for sequencing nucleic acid molecules, the method comprising: directing the processing of a first plurality of nucleic acid molecules to generate a first plurality of libraries for performing an unbiased sequencing; directing the processing of a second plurality of nucleic acid molecules to generate a second plurality of libraries for performing a biased sequencing; directing the pooling the first plurality of libraries and the second plurality of libraries to generate a pooled plurality of libraries; generating, from the pooled plurality of libraries, a first plurality of sequencing reads corresponding to the first plurality of nucleic acid molecules; and generating, from the pooled plurality of libraries, a second plurality of sequencing reads corresponding to the second plurality of nucleic acid molecules.

Another aspect of the present disclosure provides a non-transitory computer-readable medium comprising machine-executable code that, upon execution by a computer processor, implements a method for sequencing nucleic acid molecules, the method comprising: directing the processing of a first plurality of nucleic acid molecules to generate a first plurality of libraries for performing a first biased sequencing; directing the processing of a second plurality of nucleic acid molecules to generate a second plurality of libraries for performing a second biased sequencing; directing the pooling the first plurality of libraries and the second plurality of libraries to generate a pooled plurality of libraries; generating, from the pooled plurality of libraries, a first plurality of sequencing reads corresponding to the first plurality of nucleic acid molecules; and generating, from the pooled plurality of libraries, a second plurality of sequencing reads corresponding to the second plurality of nucleic acid molecules.

Another aspect of the present disclosure provides a non-transitory computer-readable medium comprising machine-executable code that, upon execution by a computer processor, implements a method for sequencing nucleic acid molecules, the method comprising: directing the processing of a first plurality of nucleic acid molecules to generate a first plurality of libraries for performing a first unbiased sequencing; directing the processing of a second plurality of nucleic acid molecules to generate a second plurality of libraries for performing a second unbiased sequencing; directing the pooling the first plurality of libraries and the second plurality of libraries to generate a pooled plurality of libraries; generating, from the pooled plurality of libraries, a first plurality of sequencing reads corresponding to the first plurality of nucleic acid molecules; and generating, from the pooled plurality of libraries, a second plurality of sequencing reads corresponding to the second plurality of nucleic acid molecules.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious aspects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications, patents and patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
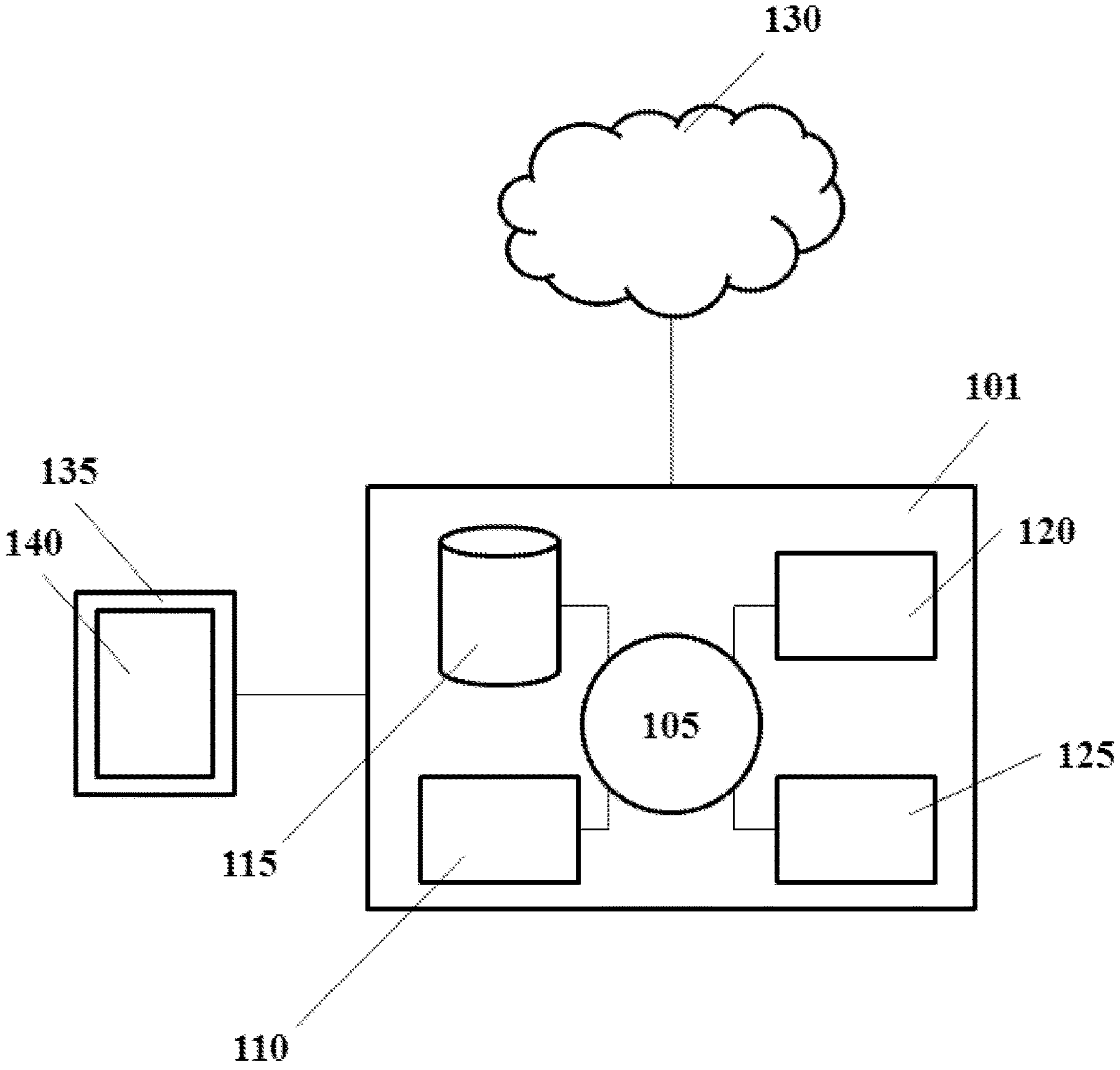
FIG. 1 shows a computer system that is programmed or otherwise configured to implement methods or systems provided herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nucleic acid," or "polynucleotide," as used herein, generally refers to a molecule comprising nucleic acid subunits, or nucleotides. A nucleic acid may include nucleotides selected from adenosine (A), cytosine (C), guanine (G), thymine (T), and uracil (U), or variants thereof. A nucleotide generally includes a nucleoside and at least 1, 2, 3, 4, 5, 6, 7, 8, 9, 10, or more phosphate ($PO_3$) groups. A nucleotide may include a nucleobase, a five-carbon sugar (either ribose or deoxyribose), and phosphate groups.

Ribonucleotides are nucleotides in which the sugar is ribose. Deoxyribonucleotides are nucleotides in which the sugar is deoxyribose. A nucleotide may be a nucleoside monophosphate or a nucleoside polyphosphate. A nucleotide may be a deoxyribonucleoside polyphosphate, such as, e.g., a deoxyribonucleoside triphosphate (dNTP), which may be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide may include any subunit that may be incorporated into a growing nucleic acid strand. Such subunit may be an A, C, G, T, or U, or any other subunit that is specific to complementary A, C, G, T, or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double stranded. In some examples, a nucleic acid molecule is circular.

The terms "nucleic acid molecule," "nucleic acid sequence," "nucleic acid fragment," "oligonucleotide," and "polynucleotide," as used herein, generally refer to a polynucleotide that may have various lengths, such as either deoxyribonucleotides or ribonucleotides (RNA), or analogs thereof. A nucleic acid molecule may have a length of at least about 10 bases, 20 bases, 30 bases, 40 bases, 50 bases, 100 bases, 200 bases, 300 bases, 400 bases, 500 bases, 1 kilobase (kb), 2 kb, 3 kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation may be input into databases in a computer having a central processing unit and used for bioinformatics applications such as functional genomics and homology searching. Oligonucleotides may include non-standard nucleotide(s), nucleotide analog(s), and/or modified nucleotides.

The term "sample," as used herein, generally refers to a biological sample. Examples of biological samples include nucleic acid molecules, amino acids, polypeptides, proteins, carbohydrates, fats, or viruses. In some cases, the sample contains a target nucleic acid molecule. In an example, a biological sample is a nucleic acid sample including nucleic acid molecule(s). In some examples, the biological sample is a nucleic acid sample including target nucleic acid molecule (s). The target nucleic acid molecules may be cell-free or cell-free nucleic acid molecules, such as cell-free DNA or cell-free RNA. The target nucleic acid molecules may be derived from a variety of sources including human, mammal, non-human mammal, ape, monkey, chimpanzee, reptilian, amphibian, or avian, sources. Further, samples may be extracted from variety of animal fluids containing cell-free sequences, including but not limited to blood, serum, plasma, vitreous, sputum, urine, tears, perspiration, saliva, semen, mucosal excretions, mucus, spinal fluid, amniotic fluid, lymph fluid- and the like. Cell-free polynucleotides may be fetal in origin (via fluid taken from a pregnant subject), or may be derived from tissue of the subject itself.

The term "subject," as used herein, generally refers to an individual having a biological sample that is undergoing processing or analysis. A subject can be an animal or plant. The subject can be a mammal, such as a human, dog, cat, horse, pig or rodent. The subject can be a patient, e.g., have or be suspected of having a disease, such as one or more cancers, one or more infectious diseases, one or more genetic disorder, or one or more tumors, or any combination thereof. For subjects having or suspected of having one or more tumors, the tumors may be of one or more types.

The terms "amplifying," "amplification," and "nucleic acid amplification" are used interchangeably and generally refer to generating copies of a nucleic acid. For example, "amplification" of DNA generally refers to generating copies of a DNA molecule. Moreover, amplification of a nucleic acid may be linear, exponential, or a combination thereof. Amplification may be emulsion based or may be non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification, and multiple displacement amplification (MDA). Where PCR is used, any form of PCR may be used, with non-limiting examples that include real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, mini-primer PCR, multiplex PCR, nested PCR, overlap-extension PCR, thermal asymmetric interlaced PCR and touchdown PCR. Moreover, amplification may be conducted in a reaction mixture comprising various components (e.g., a primer(s), template, nucleotides, a polymerase, buffer components, co-factors, etc.) that participate or facilitate amplification. In some cases, the reaction mixture comprises a buffer. Non-limiting examples of such buffers include magnesium-ion buffers, manganese-ion buffers and iso-citrate buffers. Additional examples of such buffers are also described in Tabor, S. et al. C.C. PNAS, 1989, 86, 4076-4080 and U.S. Pat. Nos. 5,409,811 and 5,674,716, each of which is herein incorporated by reference in its entirety.

The term "sequencing," as used herein, generally refers to generating or identifying the sequence of nucleic molecules. Sequencing may be single-molecule sequencing or sequencing by synthesis. Sequencing may be massively parallel array sequencing (e.g., Illumina™ sequencing), which may be performed using template nucleic acid molecules immobilized on a support, such as a flow cell. For example, sequencing may comprise a first-generation sequencing method, such as Maxam-Gilbert or Sanger sequencing, or a high-throughput sequencing (e.g., next-generation sequencing or NGS) method. A high-throughput sequencing method may sequence simultaneously (or substantially simultaneously) at least about 10,000, 100,000, 1 million, 10 million, 100 million, 1 billion, or more polynucleotide molecules. Sequencing methods may include, but are not limited to: pyrosequencing, sequencing-by-synthesis, single-molecule sequencing, nanopore sequencing, semiconductor sequencing, sequencing-by-ligation, sequencing-by-hybridization, Digital Gene Expression (Helicos™), massively parallel sequencing, e.g., Helicos™, Clonal Single Molecule Array (Solexa/Illumina™), sequencing using PacBio™, SOLiD™, Ion Torrent™, or Nanopore™ platforms.

The term "support," as used herein, generally refers to a solid support such as a slide, a bead, a resin, a chip, an array, a matrix, a membrane, a nanopore, or a gel. The solid support may, for example, be a bead on a flat substrate (such as glass, plastic, silicon, etc.) or a bead within a well of a substrate. The substrate may have surface properties, such as textures, patterns, microstructure coatings, surfactants, or any combination thereof to retain the bead at a desire location (such as in a position to be in operative communication with a detector). The detector of bead-based supports may be configured to maintain substantially the same read rate independent of the size of the bead. The support may be a flow cell or an open substrate. Furthermore, the support may comprise a biological support, a non-biological support, an organic support, an inorganic support, or any combination thereof. The support may be in optical communication with the detector, may be physically in contact with the detector, may be separated from the detector by a distance, or any combination thereof. The support may have a plurality of independently addressable locations. The nucleic acid molecules may be immobilized to the support at a given independently addressable location of the plurality of independently addressable locations. Immobilization of each of the plurality of nucleic acid molecules to the support may be aided by the use of an adaptor. The support may be optically coupled to the detector. Immobilization on the support may be aided by an adaptor.

The term "flow cell" as used herein, generally refers to a support which contains small fluidic channels through which substances may be pumped. Such substances may be polymerases, nucleic acid molecules and buffers. In some examples, the support may be functionalized. "Flow cell" may also generally refer to a vessel having a chamber where a reaction can be carried out, an inlet for delivering reagents to the chamber, and an outlet for removing reagents from the chamber. In some embodiments, the chamber is configured for detection of the reaction that occurs in the chamber (e.g., on a surface that is in fluid contact with the chamber). For example, the chamber can include one or more transparent surfaces allowing optical detection of arrays, optically labeled molecules, or the like, in the chamber. Examples of flow cells include, but are not limited to those used in a nucleic acid sequencing apparatus, such as flow cells for the Genome Analyzer®, MiSeq®, NextSeq®, HiSeq®, or NovaSeq™ platforms commercialized by Illumina, Inc. (San Diego, CA); or for the SOLiD™ or Ion Torrent™ sequencing platform commercialized by Life Technologies (Carlsbad, CA).

The term "detector," as used herein, generally refers to a device, generally including optical and/or electronic components that can detect signals.

The term "whole genome sequencing (WGS)," as used herein, generally refers to a process whereby the sequence of the entire genome of an organism may be determined. Such an organism may be humans, animals, viruses, or bacteria.

Sequencing coverage generally describes the average number of reads that align to known reference bases. Sequencing coverage requirements may vary by application. In some examples, the depth of coverage may be about 0.1×, 0.5×, 1×, 2×, 3×, 4×, 5×, 6×, 7×, 8×, 9×, 10×, or more than about 10×. In some examples the depth of coverage may be about 10×, 15×, 20×, 25×, 30×, 35×, 40×, 45×, 50×, 60×, 70×, 80×, 90×, 100×, or more than about 100×.

The term "targeted sequencing," as used herein, generally refers to the process of sequencing a subset of genes or regions of a genome. For example, a plurality of nucleic acid molecules corresponding to a subset of genes or genomic regions may be isolated, enriched, and/or amplified prior to the sequencing. In some examples, exomes, specific genes of interest, targets within genes, or mitochondrial DNA are sequenced. For example, a plurality of nucleic acid molecules corresponding to the specific genes of interest, targets within genes, or mitochondrial DNA may be isolated, enriched, and/or amplified prior to the sequencing.

The term "target capture panel," as used herein, generally refers to panels which contain a select set of genes or genomic regions (e.g., genetic loci) known or suspected to have associations with certain diseases or phenotypes.

The term "genetic loci," as used herein, generally refers to locations on a chromosome or any region of genomic nucleic acid molecules that is considered to be discrete genetic units for the purpose of formal linkage analysis or molecular genetic studies.

The term "bisulfite sequencing," as used herein, generally refers to a sequencing method that comprises the treatment of nucleic acid molecules with bisulfite (e.g., to selectively convert unmethylated cytosine residues of DNA molecules to uracil, while leaving methylated cytosine (5-methylcytosine) residues intact). Bisulfite sequencing may be used to detect methylation patterns in nucleic acid molecules (e.g., at a single-nucleotide resolution).

The term "control libraries," as used herein, generally refers to a library of nucleic acid molecules used to process a sample of nucleic acid molecules to generate a plurality of sequencing reads. In some examples, the control libraries are generated using unbiased sequencing. In some examples, the control libraries are generated using biased sequencing.

The term "polymerase," as used herein, generally refers to any enzyme capable of catalyzing a polymerization reaction. Examples of polymerases include, without limitation, a nucleic acid polymerase. The polymerase can be naturally occurring or synthesized. In some cases, a polymerase has relatively high processivity. An example polymerase is a Φ29 polymerase or a derivative thereof. A polymerase can be a polymerization enzyme. In some cases, a transcriptase or a ligase is used (i.e., enzymes which catalyze the formation of a bond). Examples of polymerases include a DNA polymerase, an RNA polymerase, a thermostable polymerase, a wild-type polymerase, a modified polymerase, *E. coli* DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some cases, the polymerase is a single subunit polymerase. The polymerase can have high processivity, namely the capability of the polymerase to consecutively incorporate nucleotides into a nucleic acid template without releasing the nucleic acid template. In some cases, a polymerase is a polymerase modified to accept dideoxynucleotide triphosphates, such as for example, Taq polymerase having a 667Y mutation. In some cases, a polymerase is a polymerase having a modified nucleotide binding, which may be useful for nucleic acid sequencing, with non-limiting examples that include ThermoSequenas polymerase (GE Life Sciences), AmpliTaq FS (ThermoFisher) polymerase and Sequencing Pol polymerase (Jena Bioscience). In some cases, the polymerase is genetically engineered to have discrimination against dideoxynucleotides, such, as for example, Sequenase DNA polymerase (ThermoFisher).

Complexity of Biased Samples

When biasing a sequencing library based on a sample, confidence can be gained around a particular region of interest, but in some cases, the biasing can lead to issues for algorithms that a sequencer uses to sequence the sample. For example, in some Illumina sequencing technologies, there are specific, tailored filters that are designed around the initial sequencing cycles (e.g., the first through fifth cycles of sequencing, the first 25 cycles of sequencing, etc.). In some examples, if the computer on the sequencer detects too many bases that are the same in the initial cycles (e.g., within the first five cycles), it can lead to a crash of the sequencing run. As such, in some examples, if biased samples are primarily run on a sequencer, and if the bases in the initial (e.g., the first five cycles) are too similar, where the majority of the flow cell is the same base, that can create conflict in identifying individual bases in that flow cell. However, by adding complexity, one can address this issue and prevent loss of information.

In some examples, to address this loss of information, a standard control such as phiX reference genome may be run along with a biased sample. The addition of the standard control may be used to break up the monotony on the flow cell. In this way, the added complexity may prevent the same base from occurring over a great amount of the flow cell and causing problems in determining the sequencing reads. In particular, by utilizing the control, a different base such as from the phiX genome may be added which breaks up the monotony in the imaging process during sequencing of a sample of interest. This, in turn, may allow the sequencing algorithm to continue working so as to generate the deep sequencing information around the targeted genomic region of interest.

A possible disadvantage of the use of a phiX control, however, is the amount of sequencing data that can be generated but for the loss of space that is dedicated to the phiX control on a flow cell. While the use of a phiX control may work to increase complexity so as to ensure deep sequencing of particular regions of interest, the loss of real estate on the flow cell can decrease the efficiency of, and thereby increase the cost of, sequencing a particular sample and/or represent a diminished capacity of sequencing unbiased samples of interest.

In methods and systems described herein, biased and unbiased libraries may be combined so as to generate a degree of complexity, while also providing the desired run depths of the samples. By combining biased and unbiased samples, sequencer real estate devoted to the unbiased samples that are used to increase complexity may result in desirable sequencing results. In this way, desired complexity may be achieved so as to allow sequencing of biased samples to a desired depth, while also generating desirable sequencing results of unbiased samples.

In some examples, complexity may relate to a number of unique molecules within a sequencing library. In some examples, complexity may relate to a diversity of molecules within a sequencing library. Within each strand of each molecule present on a flow cell, e.g., there may be regions that are conserved, and more specifically the initial bases that are read, such as about 75 bases being read along that molecule, and the first 5 to 20 bases, may be highly conserved, such that a high number of clusters may be lost if they similarly light up to an imaging camera. For example, when too many molecules are lit up, then a camera that is imaging the sample may not be able to distinguish particular molecules within the sample, which may all appear the same to the camera. Additionally, depending on the assay, there may be variable guidelines on how much additional diversity needs to be added. For example, in a standard sequencing run of a biased library, there may be guidelines that recommend adding 5-10% diversity such as by using a phiX genome, to the sequencing run. In other applications, such as methylation-based sequencing, methylseq, a user may need to add 20-30% diversity by use of the phiX genome. Therefore, the amount of capacity needed to introduce diversity may be variable depending on the assay being run, and may also be dependent on the sample and how much conservation is present within the molecules being analyzed.

In some examples, where a sequencer may have a larger amount of data available, more than one biased sample and/or more than one unbiased sample may be incorporated into the combined pool of samples. In some embodiments, by running a set of biased and unbiased samples together, enough complexity may be generated within the flow cell so as to allow for a sequencer to complete its run successfully, while also obtaining a desired depth around both the biased and unbiased samples. In this way, not only is desired complexity accomplished, but data is able to be obtained from two or more types of sequencing libraries without the loss of real estate on the flow cell to negligible sequencing (e.g., sequencing of a control bacteriophage).

Methods

The present disclosure provides methods for sequencing nucleic acid molecules by using pooled libraries of nucleic acid molecules. When preparing a sequencing library, it may be important to obtain as high of a complexity level as reasonably possible or practical. Library complexity may refer to the number of unique molecules in the library that are sampled by finite sequencing. In some examples, particular methods that may be used prior to and during preparation of a sequencing library may reduce sample complexity. For example, sample complexity may be reduced by increasing duplicates. In some embodiments, PCR and other biasing methods can reduce sample complexity.

In some cases, at least two libraries of nucleic acid molecules are used. Each library of nucleic acid molecules may be processed for performing either unbiased or biased sequencing. In some cases, an unbiased sequencing library may be generated using a whole genome approach. In some cases, an unbiased sequencing library may be generated using a shotgun sequencing approach. In some cases, an unbiased sequencing library may be generated by taking a human sample, and prepare the DNA for sequencing independent of a particular targeted region of the genome.

In some cases, a biased sequencing library may be generated by specifically targeting particular regions in the genome. For example, in certain embodiments where additional sequencing depth is beneficial so as to increase confidence in assessing particular mutations (e.g., single nucleotide polymorphisms (SNPs), copy number variations (CNVs), insertions or deletions (indels), or fusions), a biased library may be generated. In some embodiments, a biased library may be generated by first generating an unbiased library and then biasing the generated unbiased library using a targeted pull down. In some cases, target-specific primers may pull down the region of interest and untargeted regions may be discarded, thereby generating a biased library. In some embodiments, a biased library may be generated using an amplicon-based polymerase chain reaction (PCR) approach. In this case, a sample of interest may be taken and a PCR-based approach may be used for regions that are of interest, thereby generating a biased library.

Once distinct libraries are generated, the libraries may be pooled together. When performing this pooling of libraries, one consideration that may be taken into account is mass. When considering mass, it may be important to consider whether there are enough reads to cover both biased and unbiased samples. In some embodiments, mass may be considered by normalizing samples to the same concentration, e.g., the same number of molecules. For example, given a number of biased samples having a same or similar concentration, a pool of the biased samples may be generated where the pool has a same or similar concentration as the individual biased samples. In addition to pooling samples with the same, or similar, concentrations so as to generate a pooled sample having a desired concentration, samples may also be pooled so as to ensure sufficient reads of the samples. In particular, when an unbiased library and a biased library are pooled, the percentage contributed from each library may be designed so as to ensure sufficient sequencing reads for each of the biased samples as well as each of the unbiased samples.

In some embodiments, the percentage of unbiased samples versus biased samples may be flexible depending on the application. In some biased targeted panel sets, a larger panel of biased samples may be provided such that more reads may need to be allocated to the biased samples. In this case, unbiased shotgun samples may be run at a lower depth, such that fewer reads are allocated to the unbiased samples. Conversely, in some embodiments, a small targeted biased panel may be provided so the percentage of reads allocated to the total sequencing run may only comprise as much as 10%, thereby leaving 90% available to use for a deeper unbiased approach.

In some embodiments, a percentage of contribution attributable to components of the pooled libraries may be adjustable. Additionally, in some examples two or more fixed biased pools may be provided with two different panel sets, respectively. In examples, an unbiased sample may be run along the two fixed biased pools. In some examples, the two fixed biased pools may be run together without the need of an unbiased pool. In some examples, two fixed unbiased pools may be provided with two different panel sets, and with no additional contribution from a biased pool. In these ways, different applications can use pools combined at variable percentages based on the samples and the application in order to achieve the appropriate/desired depth of sequencing across and within various sample types.

In some cases, each library of nucleic acid molecules may be processed for performing the same type of sequencing as other libraries of nucleic acid molecules. In some cases, each library of nucleic acid molecules may be processed for performing a different type of sequencing to at least one other library of nucleic acid molecules. This may address issues associated with the efficiency and cost of whole genome sequencing.

Methods of the disclosure can comprise pooling two or more nucleic acid libraries. In some cases, at least about 2, 3, 4, 5, 6, 7, 8, 9, 10, 20, 30, 40, 50, or more than 50 libraries can be pooled in order to achieve sufficient complexity on the flow cell, to maximize use of sequencing capacity, or a combination thereof.

Non-limiting examples of libraries that can be pooled with the methods of the disclosure include WGS library, targeted library, methylation-Seq library, RNA-seq library, biased RNA library, and any combination thereof. In some cases, a WGS library is pooled with a targeted library. In some cases, a WGS library is pooled with a methylation-seq library. In some cases, a RNA-seq library is pooled with a biased RNA library. In some cases, a WGS library is pooled with a RNA-seq library, In some cases, a RNA-seq library is pooled with a methyl-seq library.

Sequencing of Pooled Biased and Unbiased Libraries

In an aspect, disclosed herein is a method for sequencing nucleic acid molecules. The method may comprise processing a first plurality of nucleic acid molecules. This may generate a first plurality of libraries for performing an unbiased sequencing. The method may comprise processing a second plurality of nucleic acid molecules. This may generate a second plurality of libraries for performing a biased sequencing. The method may comprise pooling the first plurality of libraries and the second plurality of libraries to generate a pooled plurality of libraries. The method may use a single flow cell of a sequencing platform to sequence the pooled plurality of libraries. This may generate a first plurality of sequencing reads corresponding to the first plurality of nucleic acid molecules and a second plurality of sequencing reads corresponding to the second plurality of nucleic acid molecules.

In some embodiments, pooling the first and second pluralities of libraries may increase complexity of the pooled plurality of libraries relative to at least one of the first and second plurality of libraries. In some embodiments, pooling the first and second plurality of libraries may increase complexity of the pooled plurality of libraries relative to at least one of the first and second plurality of libraries by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 50%, 55%, 60%, 65%, 70%, 75%, 80%, 85%, 90%, 95%, 100%, 125%, 150%, 175%, 200%, 250%, or greater than 250%.

In some embodiments, the first and second pluralities of nucleic acid molecules may be sourced from a same sample. In some embodiments, the first and second pluralities of nucleic acid molecules may be sourced from samples from a same patient. In some embodiments, the first and second pluralities of nucleic acid molecules may be sourced from samples from patients from a same family. In some embodiments, the first and second pluralities of nucleic acid molecules may be sourced from samples from patients from a same race or ethnicity. In some embodiments, the first and second pluralities of nucleic acid molecules may be sourced from samples from patients from a same sex or gender.

In some embodiments, where the first and second pluralities of nucleic acid molecules are from a same sample, a portion of the sample may be processed into a first plurality of nucleic acid molecules within a biased library, and a second portion of the sample may be processed into a second plurality of nucleic acid molecules within an unbiased library. In this approach, portions of the first and second pluralities of nucleic acid molecules may be combined on a sequencer and may be sequenced.

In some embodiments, a single unbiased library may be used as a control for the sequencing of each biased library. In some embodiments, a plurality of biased libraries may be sequenced together along with a control unbiased library. In some embodiments, a general sequencing control may be provided by generating a control from a known sample that has undergone the same or similar steps as the biased sample. In particular, once the steps of a known sample are known, the use of a well-characterized control such as phiX may not be as beneficial in comparison, since the information gained from the known sample may also be well-characterized. Further, in some embodiments, pooled mixtures of unbiased and biased samples may be sequenced with controls for each sample such that an unbiased sample may be a control for a biased sample and/or a biased sample may be a control for an unbiased sample.

In some examples, the processing of the first plurality of nucleic acid molecules optionally involves the fragmentation of the nucleic acid molecules. In some cases, processing may not involve fragmentation, for example, for cell-free nucleic acids obtained from a subject. Fragmentation of the first plurality of nucleic acid molecules may be done by physical methods, enzymatic methods or chemical methods. Some examples of physical methods of fragmentation include, but are not limited to, acoustic shearing or sonication. Some examples of enzymatic methods include, but are not limited to, non-specific endonuclease cocktails or transposase tagmentation reactions. In some examples, the processing of the first plurality of nucleic acid molecules involves the sizing of the fragments of the first plurality of nucleic acid molecules. Preferred sizes of fragments of the first plurality of nucleic acid molecules may be less than about 50 bases, less than about 100 bases, less than about 200 bases, less than about 400 bases, less than about 600 bases, less than about 800 bases, less than about 1000 bases, about 50 bases or more, about 100 bases or more, about 200 bases or more, about 400 bases or more, about 600 bases or more, about 800 bases or more, from about 10 bases to about 1000 bases, from about 20 bases to about 800 bases, from about 30 bases to about 600 bases, from about 40 bases to about 400 bases, from about 50 bases to about 200 bases, or from about 40 bases to about 100. In some embodiments, preferred sizes of fragments of the first plurality of nucleic acid molecules may also have base lengths that are on an order of 1,000 bases; 10,000 bases; 100,000 bases; 1,000,000 bases; or more than 1,000,000 bases.

In some examples, the first plurality of nucleic acid molecules is DNA. The processing of the first plurality of nucleic acid molecules may involve the blunting and phosphorylation of the 5' end. Blunting and phosphorylation of the 5' end may be accomplished using at least one enzyme. These enzymes may be T4 polynucleotide kinase, T4 DNA polymerase, or Klenow Large Fragment. The processing of the first plurality of nucleic acid molecules may involve the A-tailing of the 3' end. The A-tailing of the 3' end may use enzymes. These enzymes may be Taq polymerase or Klenow Fragment. The processing of the first plurality of nucleic acid molecules may involve multiplexing. The processing of the first plurality of nucleic acid molecules may involve tagmentation. Tagmentation may involve the use of a transposase enzyme to simultaneously fragment and tag nucleic acid molecules.

In some examples, the first plurality of nucleic acid molecules is RNA. The processing of the first plurality of nucleic acid molecules may involve ligation with a DNA adaptor. The DNA adaptor may be an adenylated DNA adaptor with a block 3' end. The ligation may be done using truncated T4 RNA ligase 2. The processing of the first plurality of nucleic acid molecules may involve the addition of an adaptor. This adaptor may be a 5' RNA adaptor. The processing of the first plurality of nucleic acid molecules may involve hybridization of a primer. This primer may be a reverse transcription primer. The processing of the first plurality of nucleic acid molecules may be based on complementary DNA (cDNA) synthesis. This synthesis may involve, but is not limited to, using random primers or oligo-dT primers or attaching adaptors. The processing of the first plurality of nucleic acid molecules may involve, but is not limited to, using primers to initiate the cDNA synthesis. This may then involve template switching where an adaptor sequence is added to the cDNA molecules.

The processing of the first plurality of nucleic acid molecules may involve, but is not limited to, reduced amplification. The processing of the first plurality of nucleic acid molecules may involve, but is not limited to, reducing duplicate reads. The processing of the first plurality of nucleic acid molecules may involve, but is not limited to, using multiple combinations of indexed adaptors. The processing of the first plurality of nucleic acid molecules may involve, but is not limited to, mitigating batch effects. The processing of the first plurality of nucleic acid molecules may involve, but is not limited to, reducing variability in day-to-day sample processing. This may involve reducing day-to-day variability in reaction conditions, reagent batches, pipetting accuracy, and human error.

In some examples, the processing of the second plurality of nucleic acid molecules involves the fragmentation of the nucleic acid molecules. Fragmentation of the second plurality of nucleic acid molecules may be done by physical methods, enzymatic methods or chemical methods. Some examples of physical methods of fragmentation include, but are not limited to, acoustic shearing or sonication. Some examples of enzymatic methods include, but are not limited to, non-specific endonuclease cocktails or transposase tagmentation reactions. In some examples, the processing of the second plurality of nucleic acid molecules involves the sizing of the fragments of the second plurality of nucleic acid molecules. Preferred sizes of fragments of the second plurality of nucleic acid molecules may be less than about 50 bases, less than about 100 bases, less than about 200 bases, less than about 400 bases, less than about 600 bases, less than about 800 bases, less than about 1000 bases, about 50 bases or more, about 100 bases or more, about 200 bases or more, about 400 bases or more, about 600 bases or more, about 800 bases or more, from about 10 bases to about 1000 bases, from about 20 bases to about 800 bases, from about 30 bases to about 600 bases, from about 40 bases to about 400 bases, from about 50 bases to about 200 bases, or from about 40 bases to about 100.

In some examples, the second plurality of nucleic acid molecules is DNA. The processing of the second plurality of nucleic acid molecules may involve the blunting and phosphorylation of the 5' end. Blunting and phosphorylation of the 5' end may be accomplished using at least one enzyme. These enzymes may be T4 polynucleotide kinase, T4 DNA polymerase, or Klenow Large Fragment. The processing of the second plurality of nucleic acid molecules may involve the A-tailing of the 3' end. The A-tailing of the 3' end may use enzymes. These enzymes may be Taq polymerase or Klenow Fragment. The processing of the second plurality of nucleic acid molecules may involve multiplexing. The processing of the second plurality of nucleic acid molecules may involve tagmentation. Tagmentation may involve the use of a transposase enzyme to simultaneously fragment and tag nucleic acid molecules.

In some examples, the second plurality of nucleic acid molecules is RNA. The processing of the second plurality of nucleic acid molecules may involve ligation with a DNA adaptor. The DNA adaptor may be an adenylated DNA adaptor with a block 3' end. The ligation may be done using truncated T4 RNA ligase 2. The processing of the second plurality of nucleic acid molecules may involve the addition of an adaptor. This adaptor may be a 5' RNA adaptor. The processing of the second plurality of nucleic acid molecules may involve hybridization of a primer. This primer may be a reverse transcription primer. The processing of the second plurality of nucleic acid molecules may be based on cDNA synthesis. This synthesis may involve, but is not limited to, using random primers or oligo-dT primers or attaching adaptors. The processing of the second plurality of nucleic acid molecules may involve, but is not limited to, using primers to initiate the cDNA synthesis. This may then involve template switching where an adaptor sequence is added to the cDNA molecules.

The processing of the second plurality of nucleic acid molecules may involve, but is not limited to, increasing amplification. The processing of the second plurality of nucleic acid molecules may involve, but is not limited to, increasing duplicate reads. The processing of the second plurality of nucleic acid molecules may involve, but is not limited to, using minimal combinations of indexed adaptors. The processing of the second plurality of nucleic acid molecules may involve, but is not limited to, exaggerating batch effects. The processing of the second plurality of nucleic acid molecules may involve, but is not limited to, increasing variability in day-to-day sample processing. This may involve increasing day-to-day variability in reaction conditions, reagent batches, pipetting accuracy, and human error.

In some examples, the first plurality of libraries and the second plurality of libraries are pooled. A pooled plurality of libraries may be generated. Pooling may involve, but is not limited to, mixing.

In some examples, sequencing of the pooled plurality of libraries involves, but is not limited to, whole genome sequencing (WGS), de novo sequencing, mate pair sequencing, chromosome immunoprecipitation sequencing (ChIP-seq), RNA immunoprecipitation sequencing (RIP-seq), crosslinking and immunoprecipitation sequencing (CLIP-seq). Sequencing may involve, but is not limited to, flow cell sequencing. Sequencing may involve, but is not limited to, patterned flow cell sequencing.

Unbiased sequencing may comprise whole genome sequencing (WGS), de novo sequencing, mate pair sequencing, chromosome immunoprecipitation sequencing (ChIP-seq), RNA immunoprecipitation sequencing (RIP-seq), crosslinking and immunoprecipitation sequencing (CLIP-seq) and RNA sequencing (RNA-Seq). Unbiased sequencing may involve, but is not limited to, flow cell sequencing. Unbiased sequencing may involve, but is not limited to, patterned flow cell sequencing.

Biased sequencing may comprise whole genome sequencing (WGS), de novo sequencing, mate pair sequencing, chromosome immunoprecipitation sequencing (ChIP-seq), RNA immunoprecipitation sequencing (RIP-seq), crosslinking and immunoprecipitation sequencing (CLIP-seq). Biased sequencing may involve, but is not limited to, flow cell sequencing. Biased sequencing may involve, but is not limited to, patterned flow cell sequencing.

The sequencing, for example, biased, unbiased, or both, may be performed at a depth of no more than about 0.1×, no more than about 0.5×, no more than about 1×, no more than about 2×, no more than about 3×, no more than about 4×, no more than about 5×, no more than about 6×, no more than about 7×, no more than about 8×, no more than about 9×, no more than about 10×, no more than about 15×, no more than about 20×, no more than about 30×, no more than about 40×, no more than about 50×, no more than about 60×, no more than about 70×, no more than about 80×, no more than about 90×, no more than about 100×, no more than about 200×, no more than about 300×, no more than about 400×, no more than about 500×, no more than about 600×, no more than about 700×, no more than about 800×, no more than about 900×, no more than about 1000×, at least about 0.1×, at least about 0.5×, at least about 1×, at least about 2×, at least about 3×, at least about 4×, at least about 5×, at least about 6×, at least about 7×, at least about 8×, at least about 9×, at least about 10×, at least about 15×, at least about 20×, at least about 30×, at least about 40×, at least about 50×, at least about 60×, at least about 70×, at least about 80×, no more than at least about 90×, at least about 100×, at least about 200×, at least about 300×, at least about 400×, at least about 500×, at least about 600×, at least about 700×, at least about 800×, at least about 900×, at least about 1000×, at least about 2000×, at least about 3000×, at least about 4000×, at least about 5000×, at least about 6000×, at least about 7000×, at least about 8000×, at least about 9000×, or at least about 10,000×.

In some embodiments, biased sequencing may be performed at a first depth, and unbiased sequencing may be performed at a second depth. In some embodiments, the first depth may be the same or substantially similar to the second depth. In some embodiments, the first depth may be greater than the second depth. In some embodiments, the second depth may be greater than the first depth.

In some embodiments, sequencing of a first library may be performed at a first depth, and sequencing of a second library may be performed at a second depth. In some embodiments, the first depth may be the same or substantially similar to the second depth. In some embodiments, the first depth may be greater than the second depth. In some embodiments, the second depth may be greater than the first depth. In some embodiments, multiple libraries may be sequenced where one or more of the multiple libraries are sequenced at different depths.

The biased sequencing may comprise targeted sequencing of a target capture panel comprising a plurality of genetic loci. For example, the biased sequencing may comprise targeted methyl-seq. Target sequencing may comprise at least one of (i) hybridization capture approaches, (ii) micro-droplet PCT droplet libraries, (iii) custom-designed droplet libraries, and (iv) amplicon sequencing.

The unbiased sequencing may comprise bisulfite sequencing, whole genome bisulfite sequencing (WGBS), APOBEC-seq, methyl-CpG-binding domain (MBD) protein capture, methyl-DNA immunoprecipitation (MeDIP), methylation sensitive restriction enzyme sequencing (MSRE/MRE-Seq or Methyl-Seq), oxidative bisulfite sequencing (oxBS-Seq), reduced representative bisulfite sequencing (RRBS), Tet-assisted bisulfite sequencing (TAB-Seq), or similar. Treatment of nucleic acid molecules with sodium bisulfite may result in the chemical conversion of unmethylated cytosine to uracil while methylated cytosines may be protected.

The method may further comprise generating the second plurality of sequencing reads. The second plurality of sequencing reads may comprise using at least a portion of the first plurality of libraries as control libraries.

The method may further comprise pooling a third plurality of libraries to generate the pooled plurality of libraries. The third plurality of libraries may comprise control libraries for generating the first plurality of sequencing reads or the second plurality of sequencing reads.

In some examples, the first plurality of nucleic acid molecules and the second plurality of nucleic acid molecules comprise DNA molecules. In some examples, the first plurality of nucleic acid molecules and the second plurality of nucleic acid molecules comprise RNA molecules. In some examples, the first plurality of nucleic acid molecules and the second plurality of nucleic acid molecules comprise a combination of DNA and RNA molecules Sequencing the nucleic acid can be performed using any suitable method, such as next-generation sequencing. In some embodiments, sequencing the nucleic acid can be performed using chain termination sequencing, hybridization sequencing, Illumina™ sequencing, ion torrent semiconductor sequencing, mass spectrophotometry sequencing, massively parallel signature sequencing (MPSS), Maxam-Gilbert sequencing, nanopore sequencing, polony sequencing, pyrosequencing, shotgun sequencing, single molecule real time (SMRT) sequencing, SOLiD™ sequencing, universal sequencing, or any combination thereof. In some embodiments, the sequencing can comprise digital PCR. In some examples, the sequencing platform is an Illumina™ sequencer. In some embodiments, the sequencing platform comprises an output range of greater than, for example, about 2,000 million reads per flow cell. In some embodiments, the sequencing platform is a NovaSeq™.

Sequencing of Pooled Distinct Biased Libraries

In an aspect, disclosed herein is a method for sequencing nucleic acid molecules. The method may comprise processing a first plurality of nucleic acid molecules. This may generate a first plurality of libraries for performing a first biased sequencing. The method may comprise processing a second plurality of nucleic acid molecules. This may generate a second plurality of libraries for performing a second biased sequencing. The method may comprise pooling the first plurality of libraries and the second plurality of libraries to generate a pooled plurality of libraries. The method may use a single flow cell of a sequencing platform to sequence the pooled plurality of libraries. This may generate a first plurality of sequencing reads corresponding to the first plurality of nucleic acid molecules and a second plurality of sequencing reads corresponding to the second plurality of nucleic acid molecules.

In some examples, the processing of the first and second pluralities of nucleic acid molecules involves the fragmentation of the nucleic acid molecules. Fragmentation of the first and second plurality of nucleic acid molecules may be done by physical methods, enzymatic methods, or chemical methods. Some examples of physical methods of fragmentation include, but are not limited to, acoustic shearing or sonication. Some examples of enzymatic methods include, but are not limited to, non-specific endonuclease cocktails or transposase tagmentation reactions. In some examples, the processing of the first and second pluralities of nucleic acid molecules involves the sizing of the fragments of the first plurality of nucleic acid molecules. Preferred sizes of fragments of the first plurality of nucleic acid molecules may be less than about 50 bases, less than about 100 bases, less than about 200 bases, less than about 400 bases, less than about 600 bases, less than about 800 bases, less than about 1000 bases, about 50 bases or more, about 100 bases or more, about 200 bases or more, about 400 bases or more, about 600 bases or more, about 800 bases or more, from about 10 bases to about 1000 bases, from about 20 bases to about 800 bases, from about 30 bases to about 600 bases, from about 40 bases to about 400 bases, from about 50 bases to about 200 bases, or from about 40 bases to about 100.

In some examples, the first and second pluralities of nucleic acid molecules are DNA. The processing of the first and second pluralities of nucleic acid molecules may involve the blunting and phosphorylation of the 5' end. Blunting and phosphorylation of the 5' end may be accomplished using at least one enzyme. These enzymes may be T4 polynucleotide kinase, T4 DNA polymerase, or Klenow Large Fragment. The processing of the first and second pluralities of nucleic acid molecules may involve the A-tailing of the 3' end. The A-tailing of the 3' end may use enzymes. These enzymes may be Taq polymerase or Klenow Fragment. The processing of the first and second pluralities of nucleic acid molecules may involve multiplexing. The processing of the first and second pluralities of nucleic acid molecules may involve tagmentation. Tagmentation may involve the use of a transposase enzyme to simultaneously fragment and tag nucleic acid molecules.

In some examples, the first and second pluralities of nucleic acid molecules are RNA. The processing of the first and second pluralities of nucleic acid molecules may involve ligation with a DNA adaptor. The DNA adaptor may be an adenylated DNA adaptor with a block 3' end. The ligation may be done using truncated T4 RNA ligase 2. The processing of the first and second pluralities of nucleic acid molecules may involve the addition of an adaptor. This adaptor may be a 5' RNA adaptor. The processing of the first and second pluralities of nucleic acid molecules may involve hybridization of a primer. This primer may be a reverse transcription primer. The processing of the first and second pluralities of nucleic acid molecules may be based on cDNA synthesis. This synthesis may involve, but is not limited to, using random primers or oligo-dT primers or attaching adaptors. The processing of the first and second pluralities of nucleic acid molecules may involve, but is not limited to, using primers to initiate the cDNA synthesis. This may then involve template switching where an adaptor sequence is added to the cDNA molecules.

The processing of the first and second pluralities of nucleic acid molecules may involve, but is not limited to, increasing amplification. The processing of the first and second pluralities of nucleic acid molecules may involve, but is not limited to, increasing duplicate reads. The processing of the first and second pluralities of nucleic acid molecules may involve, but is not limited to, using minimal combinations of indexed adaptors. The processing of the first and second pluralities of nucleic acid molecules may involve, but is not limited to, exaggerating batch effects. The processing of the first and second pluralities of nucleic acid molecules may involve, but is not limited to, increasing variability in day-to-day sample processing. This may involve increasing day-to-day variability in reaction conditions, reagent batches, pipetting accuracy, and human error.

In some examples, the first plurality of libraries and the second plurality of libraries are pooled. A pooled plurality of libraries may be generated. Pooling may involve, but is not limited to, mixing.

In some examples, sequencing of the pooled plurality of libraries involves, but is not limited to, whole genome sequencing (WGS), de novo sequencing, mate pair sequencing, chromosome immunoprecipitation sequencing (ChIP-seq), RNA immunoprecipitation sequencing (RIP-seq), crosslinking and immunoprecipitation sequencing (CLIP-seq). Sequencing may involve, but is not limited to, flow cell sequencing. Sequencing may involve, but is not limited to, patterned flow cell sequencing.

In some examples, the first biased sequencing may comprise targeted sequencing of a first target capture panel comprising a first plurality of genetic loci. For example, the first biased sequencing may comprise targeted methyl-seq. Target sequencing may comprise at least one of (i) hybridization capture approaches, (ii) microdroplet PCT droplet libraries, (iii) custom-designed droplet libraries, and (iv) amplicon sequencing. In some examples, the second biased sequencing may comprise targeted sequencing of a second target capture panel comprising a second plurality of genetic loci. For example, the second biased sequencing may comprise targeted methyl-seq. Target sequencing may comprise at least one of (i) hybridization capture approaches, (ii) microdroplet PCT droplet libraries, (iii) custom-designed droplet libraries, and (iv) amplicon sequencing.

Sequencing of Pooled Distinct Unbiased Libraries

In an aspect, disclosed herein is a method for sequencing nucleic acid molecules. The method may comprise processing a first plurality of nucleic acid molecules. This may generate a first plurality of libraries for performing a first unbiased sequencing. The method may comprise processing a second plurality of nucleic acid molecules. This may generate a second plurality of libraries for performing a second unbiased sequencing. The method may comprise pooling the first plurality of libraries and the second plurality of libraries to generate a pooled plurality of libraries. The method may use a single flow cell of a sequencing platform to sequence the pooled plurality of libraries. This may generate a first plurality of sequencing reads corresponding to the first plurality of nucleic acid molecules and a second plurality of sequencing reads corresponding to the second plurality of nucleic acid molecules.

In some examples, the processing of the first and second plurality of nucleic acid molecules optionally involves the fragmentation of the nucleic acid molecules. In some cases, for example, for cell-free nucleic acids obtained from a subject, processing may not involve fragmentation. Fragmentation of the first and second plurality of nucleic acid molecules may be done by physical methods, enzymatic methods or chemical methods. Some examples of physical methods of fragmentation include, but are not limited to, acoustic shearing or sonication. Some examples of enzymatic methods include, but are not limited to, non-specific endonuclease cocktails or transposase tagmentation reactions. In some examples, the processing of the first and second plurality of nucleic acid molecules involves the sizing of the fragments of the first plurality of nucleic acid molecules. Preferred sizes of fragments of the first plurality of nucleic acid molecules may be less than about 50 bases, less than about 100 bases, less than about 200 bases, less than about 400 bases, less than about 600 bases, less than about 800 bases, less than about 1000 bases, about 50 bases or more, about 100 bases or more, about 200 bases or more, about 400 bases or more, about 600 bases or more, about 800 bases or more, from about 10 bases to about 1000 bases, from about 20 bases to about 800 bases, from about 30 bases to about 600 bases, from about 40 bases to about 400 bases, from about 50 bases to about 200 bases, or from about 40 bases to about 100. In some embodiments, preferred sizes of fragments of the first plurality of nucleic acid molecules may also have base lengths that are on an order of 1,000 bases; 10,000 bases; 100,000 bases; 1,000,000 bases; or more than 1,000,000 bases.

In some examples, the first and second plurality of nucleic acid molecules is DNA. The processing of the first and second pluralities of nucleic acid molecules may involve the blunting and phosphorylation of the 5' end. Blunting and phosphorylation of the 5' end may be accomplished using at least one enzyme. These enzymes may be T4 polynucleotide kinase, T4 DNA polymerase, or Klenow Large Fragment. The processing of the first and second pluralities of nucleic acid molecules may involve the A-tailing of the 3' end. The A-tailing of the 3' end may use enzymes. These enzymes may be Taq polymerase or Klenow Fragment. The processing of the first and second pluralities of nucleic acid molecules may involve multiplexing. The processing of the first and second pluralities of nucleic acid molecules may involve tagmentation. Tagmentation may involve the use of a transposase enzyme to simultaneously fragment and tag nucleic acid molecules.

In some examples, the first and second pluralities of nucleic acid molecules are RNA. The processing of the first and second pluralities of nucleic acid molecules may involve ligation with a DNA adaptor. The DNA adaptor may be an adenylated DNA adaptor with a block 3' end. The ligation may be done using truncated T4 RNA ligase 2. The processing of the first and second pluralities of nucleic acid molecules may involve the addition of an adaptor. This adaptor may be a 5' RNA adaptor. The processing of the first and second pluralities of nucleic acid molecules may involve hybridization of a primer. This primer may be a reverse transcription primer. The processing of the first and second pluralities of nucleic acid molecules may be based on cDNA synthesis. This synthesis may involve, but is not limited to, using random primers or oligo-dT primers or attaching adaptors. The processing of the first and second pluralities of nucleic acid molecules may involve, but is not limited to, using primers to initiate the cDNA synthesis. This may then involve template switching where an adaptor sequence is added to the cDNA molecules.

The processing of the first plurality of nucleic acid molecules may involve, but is not limited to, reduced amplification. The processing of the first plurality of nucleic acid molecules may involve, but is not limited to, reducing duplicate reads (e.g., generating consensus sequences) or detecting/correcting base errors in reads. The processing of the first plurality of nucleic acid molecules may involve, but is not limited to, using multiple combinations of indexed adaptors. The processing of the first plurality of nucleic acid molecules may involve, but is not limited to, mitigating batch effects. The processing of the first plurality of nucleic acid molecules may involve, but is not limited to, reducing variability in day-to-day sample processing. This may involve reducing day-to-day variability in reaction conditions, reagent batches, pipetting accuracy, and human error.

In some examples, the first unbiased sequencing comprises whole genome sequencing. In some examples, the first unbiased sequencing comprises RNA sequencing. In some examples, the first unbiased sequencing comprises whole genome sequencing and RNA sequencing. In some examples, the first unbiased sequencing comprises bisulfite sequencing, whole genome bisulfite sequencing (WGBS), APOBEC-seq, methyl-CpG-binding domain (MBD) protein capture, methyl-DNA immunoprecipitation (MeDIP), methylation sensitive restriction enzyme sequencing (MSRE/MRE-Seq or Methyl-Seq), oxidative bisulfite sequencing (oxBS-Seq), reduced representative bisulfite sequencing (RRBS), Tet-assisted bisulfite sequencing (TAB-Seq), or similar. In some examples, the second unbiased sequencing comprises RNA sequencing. In some examples, the second unbiased sequencing comprises whole genome sequencing and RNA sequencing. In some examples, the second unbiased sequencing comprises bisulfite sequencing, whole genome bisulfite sequencing (WGBS), APOBEC-seq, methyl-CpG-binding domain (MBD) protein capture, methyl-DNA immunoprecipitation (MeDIP), methylation sensitive restriction enzyme sequencing (MSRE/MRE-Seq or Methyl-Seq), oxidative bisulfite sequencing (oxBS-Seq), reduced representative bisulfite sequencing (RRBS), Tet-assisted bisulfite sequencing (TAB-Seq), or similar.

The unbiased sequencing may be performed at a depth of no more than about 0.1×, no more than about 0.5×, no more than about 1×, no more than about 2×, no more than about 3×, no more than about 4×, no more than about 5×, no more than about 6×, no more than about 7×, no more than about 8×, no more than about 9×, no more than about 10×, no more than about 15×, no more than about 20× no more than about 30×, no more than about 40×, no more than about 50×, no more than about 60×, no more than about 70×, no more than about 80×, no more than about 90×, no more than about 100×, no more than about 200×, no more than about 300×, no more than about 400×, no more than about 500×, no more than about 600×, no more than about 700×, no more than about 800×, no more than about 900×, no more than about 1000×, at least about 0.1×, at least about 0.5×, at least about 1×, at least about 2×, at least about 3×, at least about 4×, at least about 5×, at least about 6×, at least about 7×, at least about 8×, at least about 9×, at least about 10×, at least about 15×, at least about 20×, at least about 30×, at least about 40×, at least about 50×, at least about 60×, at least about 70×, at least about 80×, no more than at least about 90×, at least about 100×, at least about 200×, at least about 300×, at least about 400×, at least about 500×, at least about 600×, at least about 700×, at least about 800×, at least about 900×, at least about 1000×. at least about 2000×, at least about 3000×, at least about 4000×, at least about 5000×, at least about 6000×, at least about 7000×, at least about 8000×, at least about 9000×, or at least about 10,000×.

In some examples, the nucleic acid molecules used in the methods described herein are extracted from a sample. The sample may be a biological sample.

Systems

In another aspect, disclosed herein is a system for sequencing nucleic acid molecules. The system may comprise a controller. The system may also comprise a support operatively coupled to the controller. The controller may comprise one or more computer processors. The one or more computer processors may be individually or collectively programmed to direct the processing of a first plurality of nucleic acid molecules to generate a first plurality of libraries. This may generate a first plurality of libraries for performing an unbiased sequencing. The computer processors may be individually or collectively programmed to direct the processing of a second plurality of nucleic acid molecules to generate a second plurality of libraries. This may generate a second plurality of libraries for performing a biased sequencing. The computer processors may be individually or collectively programmed to direct the pooling of the first plurality of libraries and the second plurality of libraries. This may generate a pooled plurality of libraries. This pooled plurality of libraries may be used to generate a first plurality of sequencing reads corresponding to the first plurality of nucleic acid molecules. This pooled plurality of libraries may also be used to generate a second plurality of sequencing reads corresponding to the second plurality of nucleic acid molecules.

In another aspect, disclosed herein is a system for sequencing nucleic acid molecules. The system may comprise a controller. The system may also comprise a support operatively coupled to the controller. The controller may comprise one or more computer processors. The one or more computer processors may be individually or collectively programmed to direct the processing of a first plurality of nucleic acid molecules to generate a first plurality of libraries. This may generate a first plurality of libraries for performing a first biased sequencing. The computer processors may be individually or collectively programmed to direct the processing of a second plurality of nucleic acid molecules to generate a second plurality of libraries. This may generate a second plurality of libraries for performing a second biased sequencing. The computer processors may be individually or collectively programmed to direct the pooling of the first plurality of libraries and the second plurality of libraries. This may generate a pooled plurality of libraries. This pooled plurality of libraries may be used to generate a first plurality of sequencing reads corresponding to the first plurality of nucleic acid molecules. This pooled plurality of libraries may also be used to generate a second plurality of sequencing reads corresponding to the second plurality of nucleic acid molecules.

In another aspect, disclosed herein is a system for sequencing nucleic acid molecules. The system may comprise a controller. The system may also comprise a support operatively coupled to the controller. The controller may comprise one or more computer processors. The one or more computer processors may be individually or collectively programmed to direct the processing of a first plurality of nucleic acid molecules to generate a first plurality of libraries. This may generate a first plurality of libraries for performing a first unbiased sequencing. The computer processors may be individually or collectively programmed to direct the processing of a second plurality of nucleic acid molecules to generate a second plurality of libraries. This may generate a second plurality of libraries for performing a second unbiased sequencing. The computer processors may be individually or collectively programmed to direct the pooling of the first plurality of libraries and the second plurality of libraries. This may generate a pooled plurality of libraries. This pooled plurality of libraries may be used to generate a first plurality of sequencing reads corresponding to the first plurality of nucleic acid molecules. This pooled plurality of libraries may also be used to generate a second plurality of sequencing reads corresponding to the second plurality of nucleic acid molecules.

Software

In an aspect, described herein is a non-transitory computer-readable medium that may comprise machine-executable code. Upon execution by a computer processor, the machine-executable code may implement a method for sequencing nucleic acid molecules. The method being implemented may comprise processing a first plurality of nucleic molecules to generate a first plurality of libraries for performing an unbiased sequencing. The method being implemented may comprise processing a second plurality of nucleic acid molecules to generate a second plurality of libraries for performing a biased sequencing. The method being implemented may pool the first plurality of libraries and the second plurality of libraries. The method being implemented may generate a pooled plurality of libraries. The method being implemented may use a single flow cell of a sequencing platform to sequence the pooled plurality of libraries. The method being implemented may generate a first plurality of sequencing reads corresponding to the first plurality of nucleic acid molecules and a second plurality of sequencing reads corresponding to the second plurality of nucleic acid molecules.

In an aspect, described herein is a non-transitory computer-readable medium that may comprise machine-executable code. Upon execution by the computer processor, the machine-executable code may implement a method for sequencing nucleic acid molecules. The method being implemented may process a first plurality of nucleic acid molecules. The method being implemented may generate a first plurality of libraries for performing a first biased sequencing. The method being implemented may process a second plurality of nucleic acid molecules. The method being implemented may generate a second plurality of libraries for performing a second biased sequencing. The method being implemented may pool the first plurality of libraries and the second plurality of libraries to generate a pooled plurality of libraries. The method being implemented may use a single flow cell of a sequencing platform to sequence the pooled plurality of libraries. The method being implemented may generate a first plurality of sequencing reads corresponding to the first plurality of nucleic acid molecules and a second plurality of sequencing reads corresponding to the second plurality of nucleic acid molecules.

In an aspect, described herein is a non-transitory computer-readable medium that may comprise machine-executable code. Upon execution by one or more computer processors, the machine-executable code may implement a method for sequencing nucleic acid molecules. The method being implemented may process a first plurality of nucleic acid molecules. The method implemented may generate a first plurality of libraries for performing a first unbiased sequencing. The method being implemented may process a second plurality of nucleic acid molecules. The method being implemented may generate a second plurality of libraries for performing a second unbiased sequencing. The method being implemented may pool the first plurality of libraries and the second plurality of libraries to generate a pooled plurality of libraries. The method being implemented may use a single flow cell of a sequencing platform to sequence the pooled plurality of libraries. The method being implemented may generate a first plurality of sequencing reads corresponding to the first plurality of nucleic acid molecules and a second plurality of sequencing reads corresponding to the second plurality of nucleic acid molecules.

Computer Systems

The present disclosure provides computer systems that are programmed to implement methods of the disclosure. FIG. 1 shows a computer system 101 that is programmed or otherwise configured to implement methods and systems of the present disclosure, such as performing nucleic acid sequence and sequence analysis.

The computer system 101 includes a central processing unit (CPU, also "processor" and "computer processor" herein) 105, which can be a single core or multi core processor, or a plurality of processors for parallel processing. The computer system 101 also includes memory or memory location 110 (e.g., random-access memory, read-only memory, flash memory), electronic storage unit 115 (e.g., hard disk), communication interface 120 (e.g., network adapter) for communicating with other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 can be a data storage unit (or data repository) for storing data. The computer system 101 can be operatively coupled to a computer network ("network") 130 with the aid of the communication interface 120. The network 130 can be the Internet, an internet and/or extranet, or an intranet and/or extranet that is in communication with the Internet. The network 130 in some cases is a telecommunication and/or data network. The network 130 can include computer server (s), which can enable distributed computing, such as cloud computing. The network 130, in some cases with the aid of the computer system 101, can implement a peer-to-peer network, which may enable devices coupled to the computer system 101 to behave as a client or a server.

The CPU 105 can execute a sequence of machine-readable instructions, which can be embodied in a program or software. The instructions may be stored in a memory location, such as the memory 110. The instructions can be directed to the CPU 105, which can subsequently program or otherwise configure the CPU 105 to implement methods of the present disclosure. Examples of operations performed by the CPU 105 can include fetch, decode, execute, and writeback.

The CPU 105 can be part of a circuit, such as an integrated circuit. Other component(s) of the system 101 can be included in the circuit. In some cases, the circuit is an application specific integrated circuit (ASIC).

The storage unit 115 can store files, such as drivers, libraries and saved programs. The storage unit 115 can store user data, e.g., user preferences and user programs. The computer system 101 in some cases can include additional data storage unit(s) that is external to the computer system 101, such as located on a remote server that is in communication with the computer system 101 through an intranet or the Internet.

The computer system 101 can communicate with remote computer systems through the network 130. For instance, the computer system 101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Androidenabled device, Blackberry®), or personal digital assistants. The user can access the computer system 101 via the network 130.

Methods as described herein can be implemented by way of machine (e.g., computer processor) executable code stored on an electronic storage location of the computer system 101, such as, for example, on the memory 110 or electronic storage unit 115. The machine executable or machine readable code can be provided in the form of software. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying sequences of instructions to a processor for execution.

The computer system 101 can include or be in communication with an electronic display 135 that comprises a user interface (UI) 140 for providing, for example, results of nucleic acid sequencing (e.g., sequence reads, consensus sequences, etc.). Examples of UIs include, without limitation, a graphical user interface (GUI) and web-based user interface.

Methods and systems of the present disclosure can be implemented by way of algorithms. An algorithm can be implemented by way of software upon execution by the central processing unit 105. The algorithm can, for example, implement methods and systems of the present disclosure.

EXAMPLES

Example 1: Method of Sequencing DNA Using Unbiased/Biased Sequencing

Figure 2:
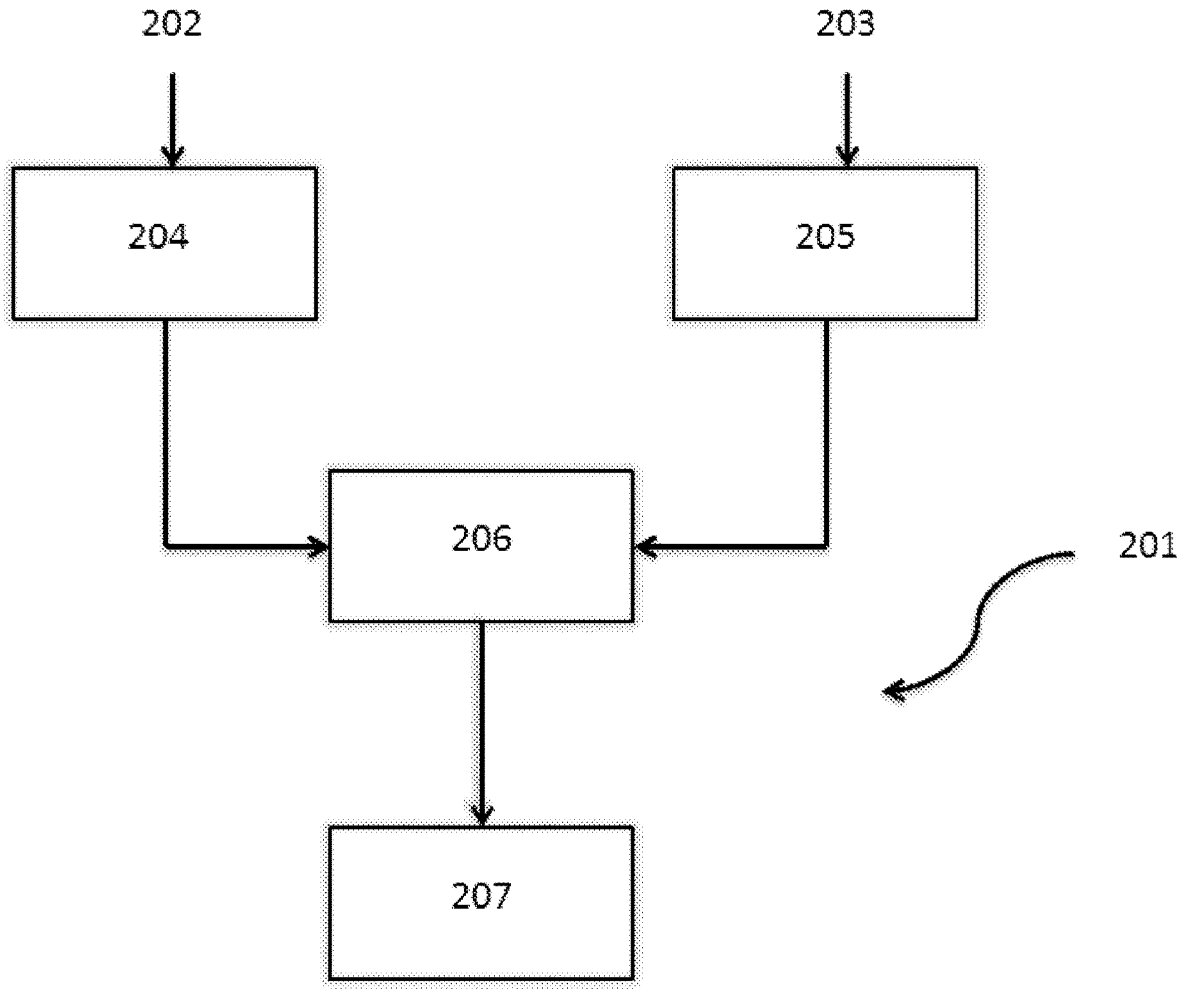
FIG. 2 shows an example of a method of sequencing nucleic acid molecules using unbiased and biased sequencing, in accordance with disclosed embodiments.

In an example, the present disclosure provides a method of sequencing DNA using libraries prepared for performing unbiased and biased sequencing (FIG. 2). DNA is extracted from tissue or cells. The extracted DNA is divided into two samples, a first sample 202 and a second sample 203.

The DNA in the first sample is then processed in operation 204. The DNA in the first sample is optionally subjected to fragmentation. Some fragmentation methods are physical methods (acoustic shearing or sonication), enzymatic methods (endonuclease cocktails or transposase tagmentation reactions), or chemical methods. The resulting DNA fragments of the first sample are sized. The sized DNA fragments of the first sample are converted into the first library by ligation to sequencing adaptors containing specific sequences designed to interact with the surface of the flow cell of a next-generation sequencing platform. Up until this point, steps have been taken to mitigate bias in the fragmentation, sizing and ligation of the DNA in the first sample.

The DNA in the second sample is then processed in operation 205. The DNA in the second sample is subjected to fragmentation. Some fragmentation methods are physical methods (acoustic shearing or sonication), enzymatic methods (endonuclease cocktails or transposase tagmentation reactions), or chemical methods. The resulting DNA fragments of the second sample are sized. The sized DNA fragments of the second sample are converted into the second library by ligation to sequencing adaptors containing specific sequences designed to interact with the surface of the flow cell of a next-generation sequencing platform. Up until this point, steps have been taken to exaggerate bias in the fragmentation, sizing, and ligation of the DNA in the second sample.

Figure 6:
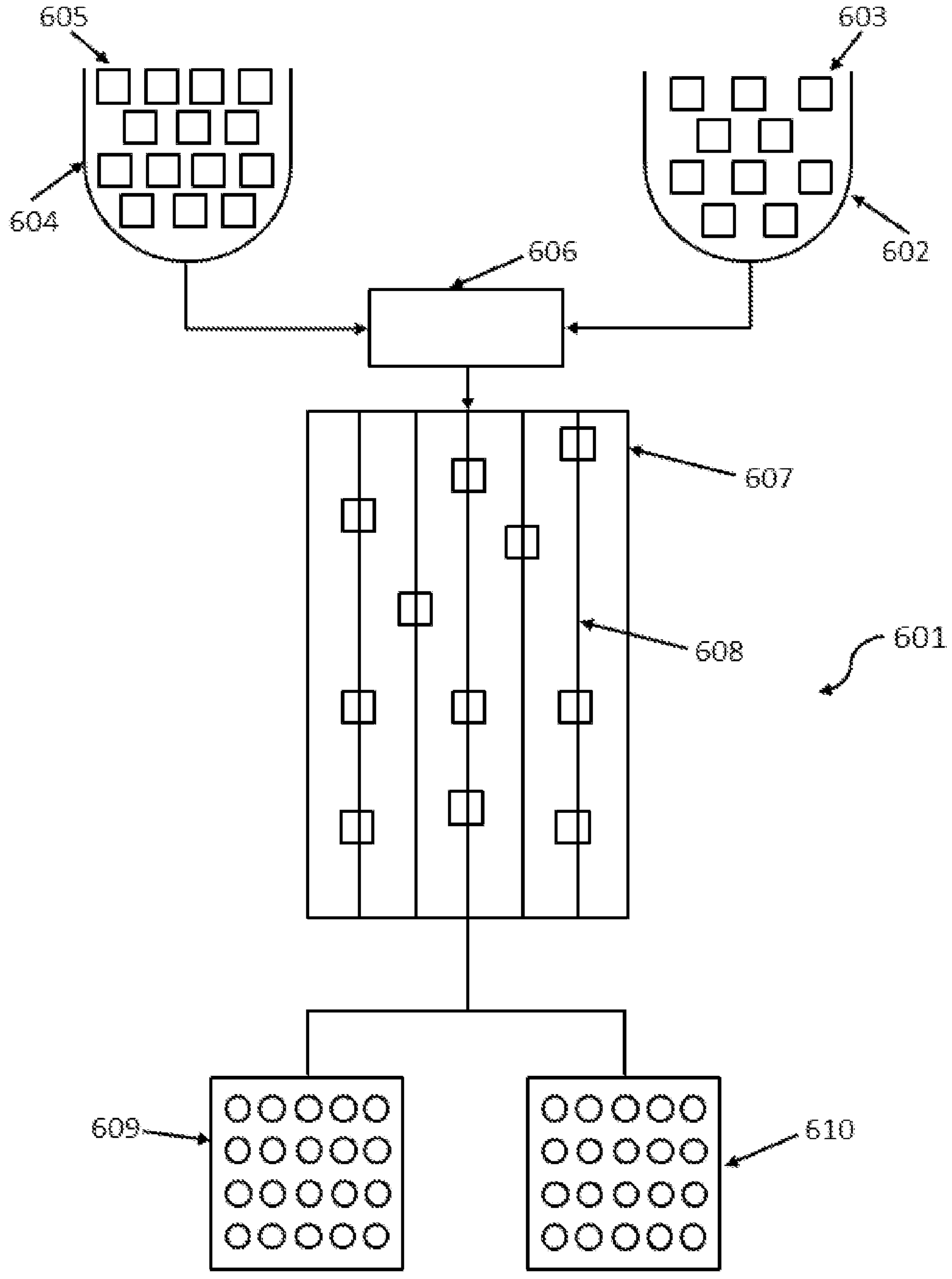
FIG. 6 shows an example of how sequencing reads obtained from nucleic acid molecules prepared for biased and/or unbiased sequencing may be correlated with the original nucleic acid molecules, in accordance with disclosed embodiments.

The first library and the second library are pooled to produce the pooled library (FIG. 6). Specifically, the processed DNA 603 of the first library 602 is pooled with the processed DNA 605 of the second library 604. The pooling of the first library 602 and the second library 602 occurs before entering the flow cell 607. The adaptors of the DNA of the first library and the DNA of the second library interact with surface of the channels in the flow cell 608. The pooled library is subjected to clonal amplification using cluster generation. The pooled library is then subjected to sequencing, for example, paired end or single read sequencing to produce sequencing reads. Sequencing reads are then correlated to the DNA of the first sample 610 and the DNA of the second sample 609.

Example 2: Method of Sequencing DNA Using Biased/Biased Sequencing

Figure 3:
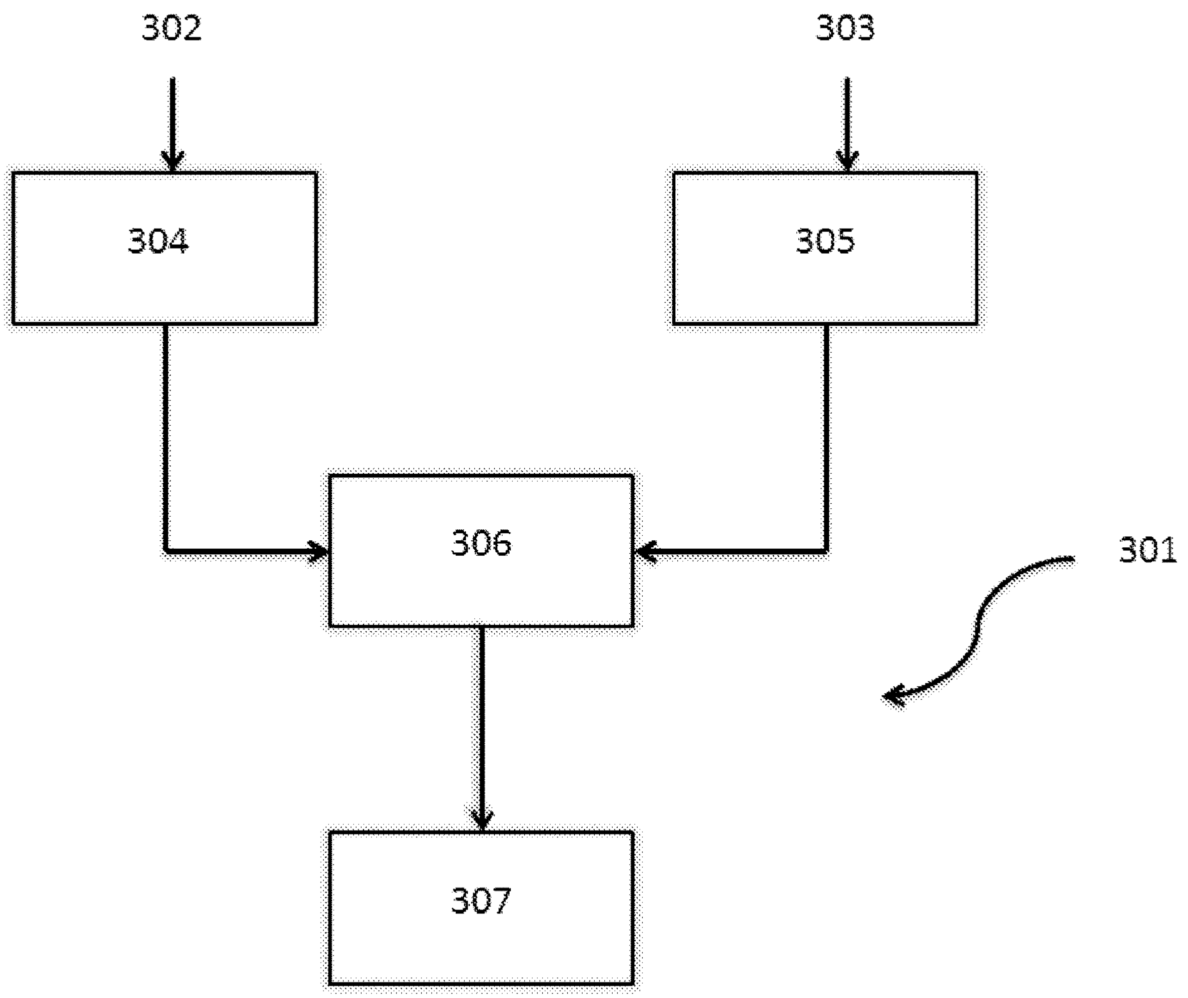
FIG. 3 shows an example of a method of sequencing nucleic acid molecules using biased sequencing, in accordance with disclosed embodiments.

In an example, the present disclosure provides a method of sequencing DNA using libraries prepared for performing unbiased and biased sequencing (FIG. 3). DNA is extracted from tissue or cells. The extracted DNA is divided into two samples, a first sample 302 and a second sample 303.

The DNA in the first sample is then processed in operation 304. The DNA in the first sample is optionally subjected to fragmentation. Some fragmentation methods are physical methods (acoustic shearing or sonication), enzymatic methods (endonuclease cocktails or transposase tagmentation reactions), or chemical methods. The resulting DNA fragments of the first sample are sized. The sized DNA fragments of the first sample are converted into the first library by ligation to sequencing adaptors containing specific sequences designed to interact with the surface of the flow cell of a next-generation sequencing platform.

The DNA in the second sample is then processed in operation 305. The DNA in the second sample is optionally subjected to fragmentation. Some fragmentation methods are physical methods (acoustic shearing or sonication), enzymatic methods (endonuclease cocktails or transposase tagmentation reactions), or chemical methods. The resulting DNA fragments of the second sample are sized. The sized DNA fragments of the second sample are converted into the second library by ligation to sequencing adaptors containing specific sequences designed to interact with the surface of the flow cell of a next-generation sequencing platform. Up until this point, steps have been taken to exaggerate bias in the fragmentation, sizing, and ligation of the DNA in the second sample.

The first library and the second library are pooled to produce the pooled library (FIG. 6). Specifically, the processed DNA 603 of the first library 602 is pooled with the processed DNA 605 of the second library 604. The pooling of the first library 602 and the second library 602 occurs before entering the flow cell 607. The adaptors of the DNA of the first library and the DNA of the second library interact with surface of the channels in the flow cell 608. The pooled library is subjected to clonal amplification using cluster generation. The pooled library is then subjected to sequencing for example, paired end or single read sequencing to produce sequencing reads. Sequencing reads are then correlated to the DNA of the first sample 610 and the DNA of the second sample 609.

Example 3: Method of Sequencing DNA Using Unbiased/Unbiased Sequencing

Figure 4:
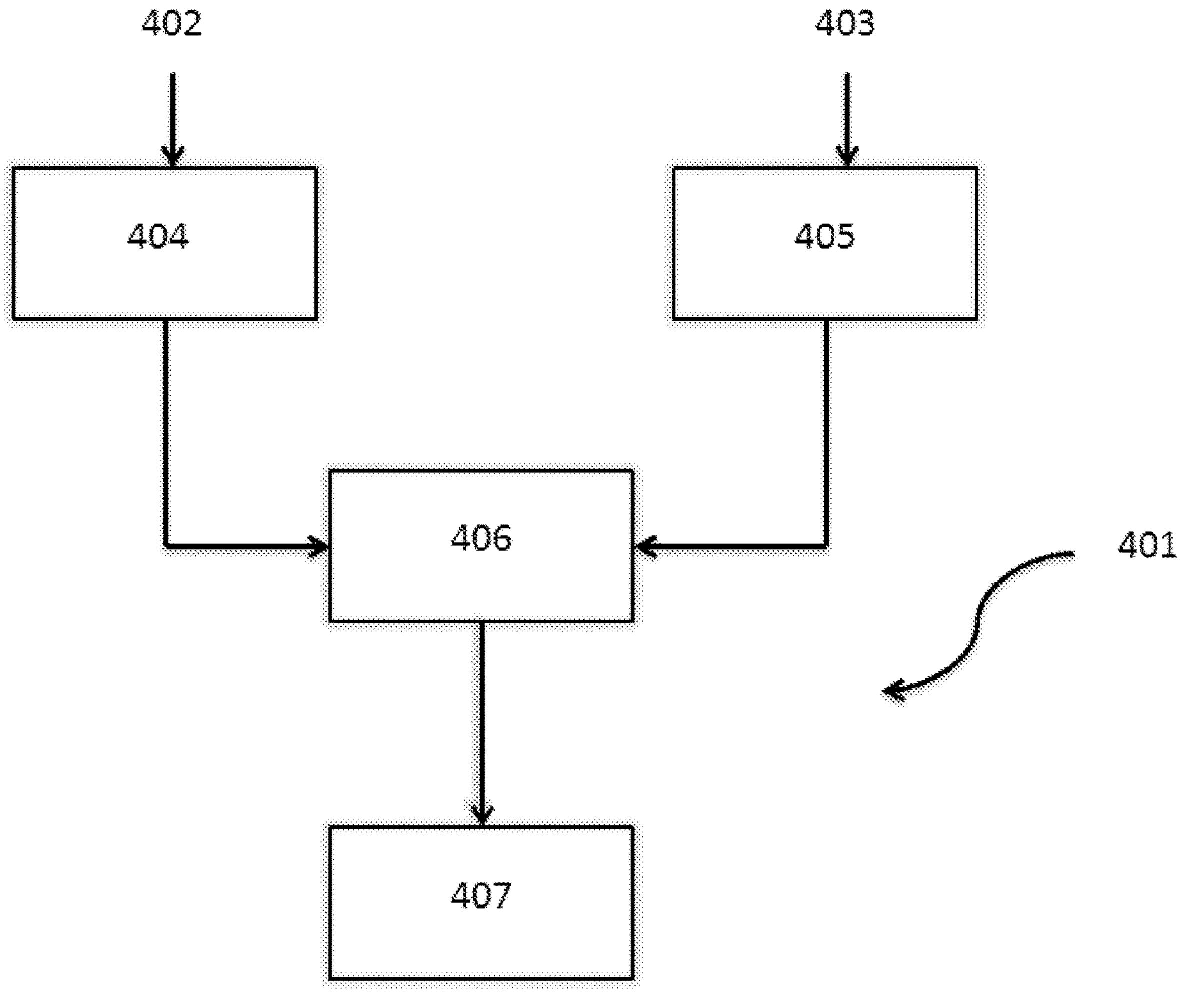
FIG. 4 shows an example of a method of sequencing nucleic acid molecules using unbiased sequencing, in accordance with disclosed embodiments.

In an example, the present disclosure provides a method of sequencing DNA using libraries prepared for performing unbiased and biased sequencing (FIG. 4). DNA is extracted from tissue or cells. The extracted DNA is divided into two samples, a first sample 402 and a second sample 403.

The DNA in the first sample is then processed in operation 404. The DNA in the first sample is optionally subjected to fragmentation. Some fragmentation methods are physical methods (acoustic shearing or sonication), enzymatic methods (endonuclease cocktails or transposase tagmentation reactions), or chemical methods. The resulting DNA fragments of the first sample are sized. The sized DNA fragments of the first sample are converted into the first library by ligation to sequencing adaptors containing specific sequences designed to interact with the surface of the flow cell of a next-generation sequencing platform. Up until this point, steps have been taken to mitigate bias in the fragmentation, sizing, and ligation of the DNA in the first sample.

The DNA in the second sample is then processed in operation 405. The DNA in the second sample is optionally subjected to fragmentation. Some fragmentation methods are physical methods (acoustic shearing or sonication), enzymatic methods (endonuclease cocktails or transposase tagmentation reactions), or chemical methods. The resulting DNA fragments of the second sample are sized. The sized DNA fragments of the second sample are converted into the second library by ligation to sequencing adaptors containing specific sequences designed to interact with the surface of the flow cell of a next-generation sequencing platform.

The first library and the second library are pooled to produce the pooled library (FIG. 6). Specifically, the processed DNA 603 of the first library 602 is pooled with the processed DNA 605 of the second library 604. The pooling of the first library 602 and the second library 602 occurs before entering the flow cell 607. The adaptors of the DNA of the first library and the DNA of the second library interact with surface of the channels in the flow cell 608. The pooled library is subjected to clonal amplification using cluster generation. The pooled library is then subjected to sequencing for example, paired end or single read sequencing to produce sequencing reads. Sequencing reads are then correlated to the DNA of the first sample 610 and the DNA of the second sample 609.

Example 4: Method of Sequencing RNA Using Unbiased/Biased Sequencing

In an example, the present disclosure provides a method of sequencing RNA using libraries prepared for performing unbiased and biased sequencing (FIG. 2). RNA is extracted from tissue or cells. The extracted RNA is divided into two samples, a first sample 202 and a second sample 203.

The RNA in the first sample is then processed in operation 204. The RNA in the first sample is optionally subjected to fragmentation. Some fragmentation methods are physical methods (acoustic shearing or sonication), enzymatic methods (endonuclease cocktails or transposase tagmentation reactions) or chemical methods. The resulting RNA fragments of the first sample are sized. The sized RNA fragments of the first sample are converted to cDNA using reverse transcription to produce the first library. Up until this point, steps have been taken to mitigate bias in the fragmentation and cDNA synthesis of the RNA in the first sample.

The RNA in the second sample is then processed in operation 205. The RNA in the second sample is optionally subjected to fragmentation. Some fragmentation methods are physical methods (acoustic shearing or sonication), enzymatic methods (endonuclease cocktails or transposase tagmentation reactions), or chemical methods. The resulting RNA fragments of the second sample are sized. The sized RNA fragments of the second sample are converted to cDNA using reverse transcription to produce the second library. Up until this point, steps have been taken to exaggerate bias in the fragmentation and cDNA synthesis of the RNA in the second sample.

The first library and the second library are pooled to produce the pooled library (FIG. 6). Specifically, the processed RNA 603 of the first library 602 is pooled with the processed RNA 605 of the second library 604. The pooling of the first library 602 and the second library 602 occurs before entering the flow cell 607. The cDNA of the first library and the cDNA of the second library interact with surface of the channels in the flow cell 608. The pooled library is subjected to clonal amplification using cluster generation. The pooled library is then subjected to sequencing for example, paired end or single read sequencing to produce sequencing reads. Sequencing reads are then correlated to the RNA of the first sample 610 and the RNA of the second sample 609.

Example 5: Method of Sequencing RNA Using Biased/Biased Sequencing

In an example, the present disclosure provides a method of sequencing RNA using libraries prepared for performing unbiased and biased sequencing (FIG. 3). RNA is extracted from tissue or cells. The extracted RNA is divided into two samples, a first sample 302 and a second sample 303.

The RNA in the first sample is then processed in operation 304. The RNA in the first sample is optionally subjected to fragmentation. Some fragmentation methods are physical methods (acoustic shearing or sonication), enzymatic methods (endonuclease cocktails or transposase tagmentation reactions), or chemical methods. The resulting RNA fragments of the first sample are sized. The sized RNA fragments of the first sample are converted to cDNA using reverse transcription to produce the first library.

The RNA in the second sample is then processed in operation 305. The RNA in the second sample is optionally subjected to fragmentation. Some fragmentation methods are physical methods (acoustic shearing or sonication), enzymatic methods (endonuclease cocktails or transposase tagmentation reactions), or chemical methods. The resulting RNA fragments of the second sample are sized. The sized RNA fragments of the second sample are converted to cDNA using reverse transcription to produce the second library. Up until this point, steps have been taken to exaggerate bias in the fragmentation and cDNA synthesis of the RNA in the second sample.

The first library and the second library are pooled to produce the pooled library (FIG. 6). Specifically, the processed RNA 603 of the first library 602 is pooled with the processed RNA 605 of the second library 604. The pooling of the first library 602 and the second library 602 occurs before entering the flow cell 607. The cDNA of the first library and the cDNA of the second library interact with surface of the channels in the flow cell 608. The pooled library is subjected to clonal amplification using cluster generation. The pooled library is then subjected to sequencing, for example, single read or paired end sequencing to produce sequencing reads. Sequencing reads are then correlated to the RNA of the first sample 610 and the RNA of the second sample 609.

Example 6: Method of Sequencing RNA Using Unbiased/Unbiased Sequencing

In an example, the present disclosure provides a method of sequencing RNA using libraries prepared for performing unbiased and biased sequencing (FIG. 4). RNA is extracted from tissue or cells. The extracted RNA is divided into two samples, a first sample 402 and a second sample 403.

The RNA in the first sample is then processed in operation 404. The RNA in the first sample is subjected to fragmentation. Some fragmentation methods are physical methods (acoustic shearing or sonication), enzymatic methods (endonuclease cocktails or transposase tagmentation reactions), or chemical methods. The resulting RNA fragments of the first sample are sized. The sized RNA fragments of the first sample are converted to cDNA using reverse transcription to produce the first library. Up until this point, steps have been taken to mitigate bias in the fragmentation and cDNA synthesis of the RNA in the first sample.

The RNA in the second sample is then processed in operation 405. The RNA in the second sample is subjected to fragmentation. Some fragmentation methods are physical methods (acoustic shearing or sonication), enzymatic methods (endonuclease cocktails or transposase tagmentation reactions), or chemical methods. The resulting RNA fragments of the second sample are sized. The sized RNA fragments of the second sample are converted to cDNA using reverse transcription to produce the second library.

The first library and the second library are pooled to produce the pooled library (FIG. 6). Specifically, the processed RNA 603 of the first library 602 is pooled with the processed RNA 605 of the second library 604. The pooling of the first library 602 and the second library 602 occurs before entering the flow cell 607. The cDNA of the first library and the cDNA of the second library interact with surface of the channels in the flow cell 608. The pooled library is subjected to clonal amplification using cluster generation. The pooled library is then subjected to sequencing for example, paired end or single read sequencing to produce sequencing reads. Sequencing reads are then correlated to the RNA of the first sample 610 and the RNA of the second sample 609.

Figure 5:
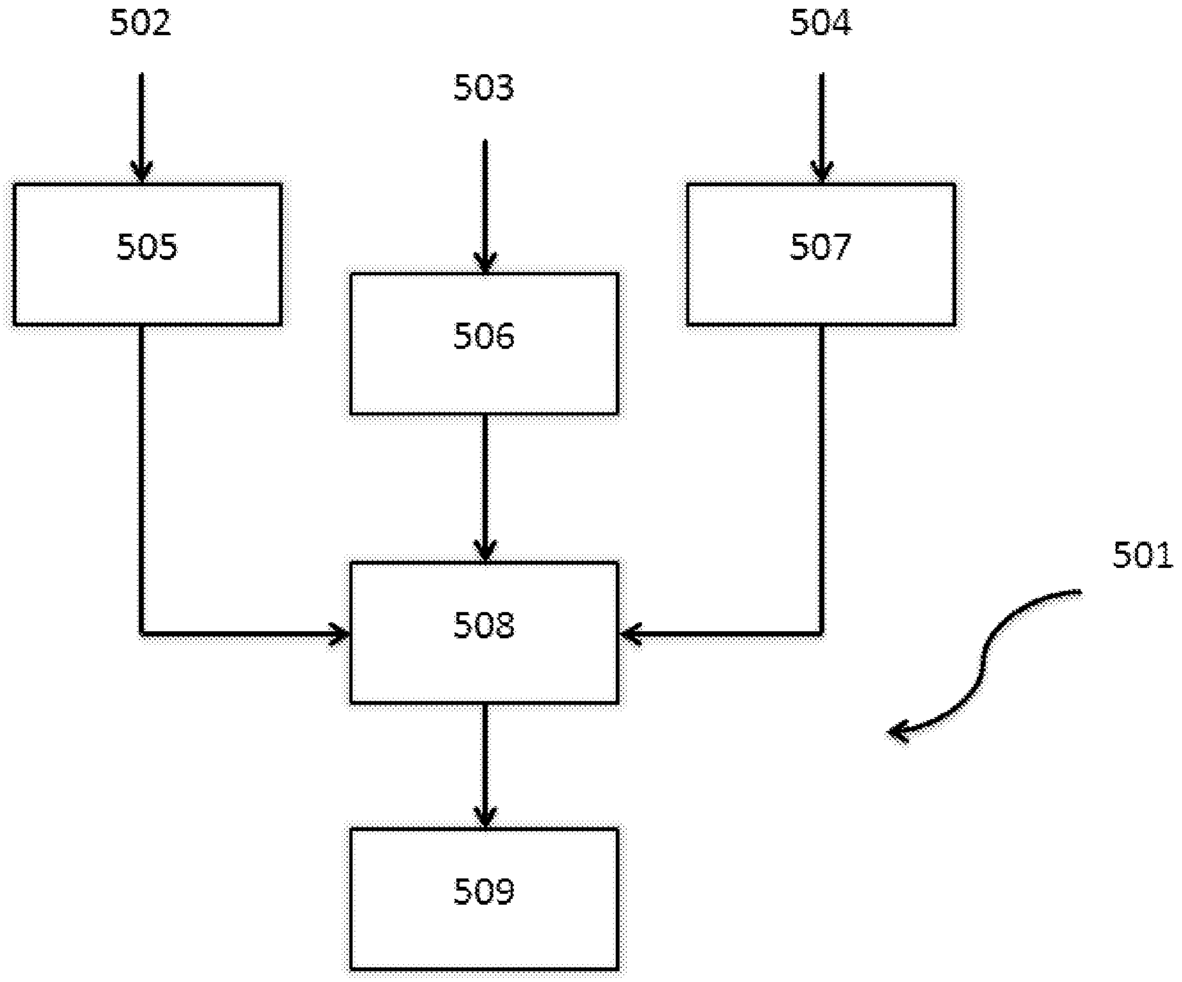
FIG. 5 shows an example of a method of sequencing nucleic acid molecules using biased and unbiased sequencing with a control library, in accordance with disclosed embodiments.

Example 7: Method of Sequencing DNA Using Unbiased/Biased/Unbiased Sequencing In an example, the present disclosure provides a method of sequencing DNA using libraries prepared for performing unbiased and biased sequencing (FIG. 5). DNA is extracted from tissue or cells. The extracted DNA is divided into three samples, a first sample 502, a second sample 503, and a third sample 504.

The DNA in the first sample is then processed in operation 505. The DNA in the first sample is optionally subjected to fragmentation. Some fragmentation methods are physical methods (acoustic shearing or sonication), enzymatic methods (endonuclease cocktails or transposase tagmentation reactions), or chemical methods. The resulting DNA fragments of the first sample are sized. The sized DNA fragments of the first sample are converted into the first library by ligation to sequencing adaptors containing specific sequences designed to interact with the surface of the flow cell of a next-generation sequencing platform. Up until this point, steps have been taken to mitigate bias in the fragmentation, sizing, and ligation of the DNA in the first sample.

The DNA in the second sample is then processed in operation 506. The DNA in the second sample is optionally subjected to fragmentation. Some fragmentation methods are physical methods (acoustic shearing or sonication), enzymatic methods (endonuclease cocktails or transposase tagmentation reactions), or chemical methods. The resulting DNA fragments of the second sample are sized. The sized DNA fragments of the second sample are converted into the second library by ligation to sequencing adaptors containing specific sequences designed to interact with the surface of the flow cell of a next-generation sequencing platform. Up until this point, steps have been taken to exaggerate bias in the fragmentation, sizing, and ligation of the DNA in the second sample.

The DNA in the third sample is then processed in operation 507. The DNA in the third sample is optionally subjected to fragmentation. Some fragmentation methods are physical methods (acoustic shearing or sonication), enzymatic methods (endonuclease cocktails or transposase tagmentation reactions), or chemical methods. The resulting DNA fragments of the third sample are sized. The sized DNA fragments of the third sample are converted into the third library by ligation to sequencing adaptors containing specific sequences designed to interact with the surface of the flow cell of a next-generation sequencing platform. Up until this point, steps have been taken to exaggerate or mitigate bias in the fragmentation, sizing, and ligation of the DNA in the third sample.

The first library, the second library, and the third library are then pooled in operation 508 to generate a pooled library. The pooled library is subjected to clonal amplification using cluster generation. The pooled library is then subjected to sequencing, for example, paired end or single read sequencing, to produce sequencing reads 509. Sequencing reads are then correlated to the DNA of the first sample, the DNA of the second sample, and the DNA of the third sample.

Example 8: Method of Sequencing RNA Using Unbiased/Biased/Unbiased Sequencing In one example, there is a method of sequencing RNA using libraries prepared for performing unbiased and biased sequencing (FIG. 5). RNA is extracted from a biological sample. The extracted RNA is divided into three samples, a first sample 502, a second sample 503, and a third sample 504.

The RNA in the first sample is then processed in operation 505. The RNA in the first sample is optionally subjected to fragmentation. Some fragmentation methods are physical methods (acoustic shearing or sonication), enzymatic methods (endonuclease cocktails or transposase tagmentation reactions), or chemical methods. The resulting RNA fragments of the first sample are sized. The sized RNA fragments of the first sample are converted into the first library by ligation to sequencing adaptors containing specific sequences designed to interact with the surface of the flow cell of a next-generation sequencing platform. Up until this point, steps have been taken to mitigate bias in the fragmentation, sizing, and ligation of the RNA in the first sample.

The RNA in the second sample is then processed in operation 506. The RNA in the second sample is optionally subjected to fragmentation. Some fragmentation methods are physical methods (acoustic shearing or sonication), enzymatic methods (endonuclease cocktails or transposase tagmentation reactions), or chemical methods. The resulting RNA fragments of the second sample are sized. The sized RNA fragments of the second sample are converted into the second library by ligation to sequencing adaptors containing specific sequences designed to interact with the surface of the flow cell of a next-generation sequencing platform. Up until this point, steps have been taken to exaggerate bias in the fragmentation, sizing, and ligation of the RNA in the second sample.

The RNA in the third sample is then processed in operation 507. The RNA in the third sample is optionally subjected to fragmentation. Some fragmentation methods are physical methods (acoustic shearing or sonication), enzymatic methods (endonuclease cocktails or transposase tagmentation reactions) or chemical methods. The resulting RNA fragments of the third sample are sized. The sized RNA fragments of the third sample are converted into the third library by ligation to sequencing adaptors containing specific sequences designed to interact with the surface of the flow cell of a next-generation sequencing platform. Up until this point, steps have been taken to exaggerate or mitigate bias in the fragmentation, sizing, and ligation of the RNA in the third sample.

The first library, the second library and the third library are then pooled in operation 508 to generate a pooled library. The pooled library is subjected to clonal amplification using cluster generation. The pooled library is then subjected to sequencing, for example, paired end or single read sequencing, to produce sequencing reads 509. Sequencing reads are then correlated to the RNA of the first sample, the RNA of the second sample, and the RNA of the third sample.

Example 9: Method of Sequencing DNA and RNA Using RNA Biased and DNA Unbiased Sequencing In an example, the present disclosure provides a method of sequencing DNA and RNA using libraries prepared for performing unbiased and biased sequencing. RNA is extracted from a biological sample. DNA is extracted from a biological sample. The biological sample can comprise cell-free nucleic acids, tissue, cells, or any combination thereof.

The extracted RNA is processed to generate a biased RNA library, such as a targeted RNA library. The extracted DNA is processed to generate an unbiased DNA library, such as a WGS library. Both libraries are prepared for running on a NGS sequencing platform, for example, by appending sequences designed to hybridize with sequences on a flow cell.

The biased RNA library and the unbiased DNA library are pooled to generate a pooled library. The pooled library is subjected to clonal amplification using cluster generation. The pooled library is then subjected to sequencing, for example, paired end or single read sequencing, to produce sequencing reads. Sequencing reads are then correlated to the RNA of the biased library and the DNA of the unbiased library.

Example 10: Method of Sequencing DNA and RNA Using DNA Biased and RNA Unbiased Sequencing In one example, there is a method of sequencing DNA and RNA using libraries prepared for performing unbiased and biased sequencing. RNA is extracted from a biological sample. DNA is extracted from a biological sample. The biological sample can comprise cell-free nucleic acids, tissue, cells, or any combination thereof.

The extracted RNA is processed to generate an unbiased RNA library, such as an RNA-seq library. The extracted DNA is processed to generate a biased DNA library, such as a targeted library. Both libraries are prepared for running on a NGS sequencing platform, for example, by appending sequences designed to hybridize with sequences on a flow cell.

The unbiased RNA library and the biased DNA library are pooled to generate a pooled library. The pooled library is subjected to clonal amplification using cluster generation. The pooled library is then subjected to sequencing, for example, paired end or single read sequencing, to produce sequencing reads. Sequencing reads are then correlated to the RNA of the unbiased library and the DNA of the biased library.

While preferred embodiments of the present invention have been shown and described herein, it will be obvious to those skilled in the art that such embodiments are provided by way of example only. It is not intended that the inventions be limited by the specific examples provided within the specification. While the inventions have been described with the reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the inventions shall also cover any such alternatives, modifications, variations, or equivalents. It is intended that the following claims define the scope of the invention and that methods and structures within the scope of these claims and their equivalents be covered thereby.

What is claimed is:

1. A method for sequencing nucleic acid molecules, comprising:

processing a first plurality of nucleic acid molecules to generate a first plurality of libraries for performing an unbiased sequencing;

processing a second plurality of nucleic acid molecules to generate a second plurality of libraries for performing a biased sequencing, wherein the biased sequencing comprises targeted sequencing of a target capture panel comprising a plurality of genetic loci, and wherein the targeted sequencing comprises targeted methylation sequencing;

pooling the first plurality of libraries and the second plurality of libraries to generate a pooled plurality of libraries; and using a single flow cell of a sequencing platform, sequencing the pooled plurality of libraries to generate a first plurality of sequencing reads corresponding to the first plurality of nucleic acid molecules and a second plurality of sequencing reads corresponding to the second plurality of nucleic acid molecules, wherein generating the second plurality of sequencing reads comprises using at least a portion of the first plurality of libraries as control libraries.

2. The method of claim 1, wherein the unbiased sequencing comprises whole genome sequencing (WGS).

3. The method of claim 2, wherein the unbiased sequencing is performed at a depth of no more than about 10×.

4. The method of claim 1, wherein the unbiased sequencing comprises methylation sequencing.

5. The method of claim 4, wherein the methylation sequencing comprises bisulfite sequencing, whole genome bisulfite sequencing (WGBS), APOBEC-seq, methyl-CpG-binding domain (MBD) protein capture, methyl-DNA immunoprecipitation (MeDIP), methylation sensitive restriction enzyme sequencing (MSRE/MRE-Seq or Methyl-Seq), oxidative bisulfite sequencing (oxBS-Seq), reduced representative bisulfite sequencing (RRBS), or Tet-assisted bisulfite sequencing (TAB-Seq).

6. The method of claim 1, wherein the first plurality of nucleic acid molecules and the second plurality of nucleic acid molecules comprise DNA molecules.

7. The method of claim 1, wherein the first plurality of nucleic acid molecules and the second plurality of nucleic acid molecules comprise RNA molecules.

8. The method of claim 1, wherein the nucleic acid molecules are extracted from a sample.

9. The method of claim 8, wherein the sample is a biological sample.

10. The method of claim 1, wherein the first plurality of nucleic acid molecules and the second plurality of nucleic acid molecules are generated from a same initial biological sample.

11. A method for sequencing nucleic acid molecules, comprising:

processing a first plurality of nucleic acid molecules to generate a first plurality of libraries for performing an unbiased sequencing:

processing a second plurality of nucleic acid molecules to generate a second plurality of libraries for performing a biased sequencing;

pooling the first plurality of libraries, the second plurality of libraries, and a third plurality of libraries to generate a pooled plurality of libraries, wherein the third plurality of libraries comprises control libraries for generating the first plurality of sequencing reads or the second plurality of sequencing reads; and using a single flow of a sequencing platform, sequencing the pooled plurality of libraries to generate a first plurality of sequencing reads corresponding to the first plurality of nucleic acid molecules and a second plurality of sequencing reads corresponding to the second plurality of nucleic acid molecules.

12. The method of claim 11, wherein the unbiased sequencing comprises whole genome sequencing (WGS).

13. The method of claim 12, wherein the unbiased sequencing is performed at a depth of no more than about 10×.

14. The method of claim 11, wherein the biased sequencing comprises targeted sequencing of a target capture panel comprising a plurality of genetic loci.

15. The method of claim 14, wherein the target sequencing comprises targeted methylation sequencing.

16. The method of claim 11, wherein the sequencing comprises methylation sequencing.

17. The method of claim 16, wherein the methylation sequencing comprising bisulfite sequencing, whole genome bisulfite sequencing (WGBS), APOBEC-seq, methyl-CpG-binding domain (MBD) protein capture, methyl-DNA immunoprecipitation (MeDIP), methylation sensitive restriction enzyme sequencing (MSRE/MRE-Seq or Methyl-Se q), oxidative bisulfite sequencing (oxBS-Seq), reduced representative bisulfite sequencing (RRBS), or Tet-assisted bisulfite sequencing (TAB-Seq).

18. The method of claim 11, wherein the first plurality of nucleic acid molecules and the second plurality of nucleic acid molecules comprises DNA molecules or RNA molecules.

19. The method of claim 11, wherein the nucleic acid molecules are extracted from a sample.

20. The method of claim 19, wherein the sample is a biological sample.

21. The method of claim 11, wherein the first plurality of nucleic acid molecules and the second plurality of nucleic acid molecules are generated from a same initial biological sample.

* * * * *